(12) United States Patent
Wellstein et al.

(10) Patent No.: US 8,420,590 B2
(45) Date of Patent: Apr. 16, 2013

(54) GENES AND PROTEINS THAT HOME TO DEVELOPING MICROVESSELS

(75) Inventors: Anton Wellstein, Washington, DC (US); Marcel O. Schmidt, Washington, DC (US); Stephan Zbinden, Wabern (CH); Mary Susan Burnett, Fairfax, VA (US); Stephen E. Epstein, Rockville, MD (US)

(73) Assignees: Georgetown University, Washington, DC (US); MedStar Health Research Institute, Inc., Washington, DC (US)

( * ) Notice: Subject to any disclaimer, the term of this patent is extended or adjusted under 35 U.S.C. 154(b) by 349 days.

(21) Appl. No.: 12/516,961

(22) PCT Filed: Nov. 30, 2007

(86) PCT No.: PCT/US2007/024629
§ 371 (c)(1),
(2), (4) Date: Mar. 8, 2010

(87) PCT Pub. No.: WO2008/069965
PCT Pub. Date: Jun. 12, 2008

(65) Prior Publication Data
US 2010/0216704 A1  Aug. 26, 2010

Related U.S. Application Data

(60) Provisional application No. 60/872,210, filed on Dec. 1, 2006, provisional application No. 60/899,899, filed on Feb. 6, 2007.

(51) Int. Cl.
*A61K 38/16* (2006.01)
*A61P 35/00* (2006.01)
*C07K 14/00* (2006.01)

(52) U.S. Cl.
USPC .......... 514/1.1; 514/13.3; 514/13.7; 530/324; 530/370

(58) Field of Classification Search .................. None
See application file for complete search history.

(56) References Cited

U.S. PATENT DOCUMENTS

2003/0113320 A1 *  6/2003  Ruoslahti et al. .......... 424/143.1

FOREIGN PATENT DOCUMENTS

| WO | WO 00/75174 | 12/2000 |
| WO | WO 2006/029343 | 3/2006 |

OTHER PUBLICATIONS

Bowie et al. Deciphering the message in protein sequences: tolerance to amino acid substitutions. Science, (Mar. 16, 1990) 247 (4948) 1306-10.*
Ngo et al., in The Protein Folding Problem and Tertiary Structure Prediction, Merz and Le Grand (Eds), Aug. 1994, Springer Verlag, pp. 433 and 492-495.*
Chavakis et al., *Role of β2-integrins for homing and neovascularization capacity of endothelial progenitor cells*, J. Exp. Med., vol. 201(1), Jan. 2005.
Database EMBL, *Human DNA sequence from clone RP4-769D20 on chromosome Xp21. 1-21.3. Contains the 5' end of four variants of the DMD gene for dystrophin (muscular dystrophy, Duchenne and Becker types)*. Sep. 22, 1998.
Buehler Alexandra et al., *cNGR: a novel homing sequence for CD13/APN targeted molecular imaging of murine cardiac angiogenesis in vivo*, Arteriosclerosis, Thrombosis, and Vascular Biology, Dec. 2006, vol. 26(12), Dec. 2006.

* cited by examiner

*Primary Examiner* — David Romeo
(74) *Attorney, Agent, or Firm* — Wolf, Greenfield & Sacks, P.C.

(57) ABSTRACT

Described herein are polypeptides that home to developing microvasculature, (also referred to as developing microvessels), such as newly developing microvasculature in mammals, particularly in humans, and to DNA that encodes such polypeptides. These polypeptides are referred to herein as developing microvasculature homing polypeptides. In a specific embodiment, the homing peptides are collateral vessel endothelia (CVE) homing polypeptides, which have been shown to home to collateral vessel endothelia after ischemia.

8 Claims, 10 Drawing Sheets

FIGURE 6A

EST sequences:

A5: SEQ ID NO.: 1

GGGGATTCAGGGGCAGTTTATAATTCAGTCACATGTTAAAGAACAAAAAGGACGAAAGAAGAATA
AAGCAGATAGAATCGTGAAATGGGTTACATTATTTGCACCATAAAGTTTAAGTAAATCAAATTAT
TGGGAATATTCTGAGATAGAGCTAAAGTCTTTCTCAAGAGTCATGGTTGAAACCACATGTTGTGG
AGGAACTGATGGTGATTGTTGCCCCATTGTGGGATTCCTCCCTATGGTAATGACATCAAAATGAA
AAAAAAAAAACACACACACACAAAAAAATGACGCAAATTGTAATTAAAGGTGGAGCTGTTTATGA
TCTGGTTATCTCCACATTGTTCTGGGAAAAAATTGAAACATTACTGGGTCAAATCATGTCTGTCA
AACAAAATGAAAGGTAAAAATAGTGAATAAAAAAAAAAAAATTAAAAACAAGCTT

A12: SEQ ID NO.: 2

GCGATTCAACACTCTATAAGAAAAAATATAATAATTTGATTTAAAAACTGGCAAAATATCTGAAT
AGATATTTCTCAAAAGAAGACATACGAATGGCAAACAAGCATACAAAAAGGTGTTCAACATCATT
GATCATCAGAGAAATGCAAATCAAAACTACAAGGAAAATATCATCTCACTCCTGTTAAAATGGCT
TTTATGCAAAAGTCAGACAATAACAAATGCTGAAAAGGATGTGGAAAAAAGGAAACCCTCATGCA
CTATTGGTGGAATGTAAATTAATACAGCCACTACGGAGAACAGTTTGCAGGTTCCTCAACAACAA
CAACAAAAAACTAAAAACAGAGCTATCTTACAATCCAACAATTCCACTCCCAGATATATATCAGA
AGTAAGGAAATGACACTAAGTTTTTGAAAAATGAAAAGCTT

B9 SEQ ID NO.: 3

GCGATTCTGGGACTGTGGATATAGCTTGCCACAGTATCTTATCAGTTAATTGCATTCTTGAATGT
GCTGGGAGTCAGCTTGCACAAGGTAAGTCCTTGAGGAAGGGGCTGCCAGTGTAAGAGCCAAGATG
GAGTCTGTCTGGCTCTCTTAGCTAAGGGAGAGTCAATTCAGGTGGAAACAAGGCTAGGTGATTAA
AGGAAAGGGAGAGTCTAAAAACAGGGTTAGTAAAAACCAGGTTGGGCATTACAGTATCACCCAGA
CAACCAAGTGTTCATGTTTAACCACAAAGCCCTCTTGTAATTGCTGAAGGGTATTTGCTTGTAAT
TGCTGCGACCATTCTTCAAGTTGTTTCTTTAACTCACATTCAAGAGTAGAAATTTGAGAAGAAAT
ACGGTTGTGATAAGCCCCTTGCAGGTGTGCTTTCACTCTCTCCCAAGCATATTGGGAGCTATTAT
ATGGCAGAGGTGTGACACAGATAGGATTATATTGCCAATCACAATGTAAATTTTGATGGGTAATG
AATGCCTGCTGCTGACCCCCCAGCCATTCAACTGCGGCTTCAAGAGCCTCCAGGTGAGACAGAAT
AGTTTTATCAATATTTACCTGTTCCTGAAATTCATGGGTTACATTATATACCATGTGGTTCACCA
CTGAGGCTATGTGAATAGATCCTGTTAGAGAGACAGCTGCAGTAGCAGCAGTTGCTAGTATGATA
ATAGCTGAGACTAAAAAGTCAATTAAAGTGGCCAGAAATCTTTTTTTCTGAGCATGAGACAGTGC
TTTTCTAAATAGCTGCTGGGTGGAATTTCCTTCCCAGCTCCAGGTTAAATTTACAGGCAGCCACA
TTTCTGCATGCCGTTTTAATCATGACGTTATACTTAACTGTGTAACGTTTTGATAACAGCATGTA
GCATACCAGTACTGGAAGACTTTATACTATACTGATTCTGTTTTTGTAACCTCGCCAAAGTATAT
GGGTGCATAGTAACACTGTCAGTATATGCAAAGTGCTGCCTTATACTCCCTAAAACAATCAGAAA

C1: SEQ ID NO.: 4

ACATTCTGTGGGATGATGGTGATGGTAGCATAGCATATGAATGTGCTTAATGCCTCTGAAGGTAG
ACTTAAAAATGGTTAAGATGCCACATTTTATGTTATGTGTATTTGATGACGATTAAACATTTTAA
AAATTGAAAAAGGTAAACATTACAAAATAATTTAGTGAAGCCAGATATCATGTCACTTCATGTTT
CTGTTAAATTTATGTACAATTAGGCTGGTTTGTATTTAGAAATTCTAGTTATAAAGATGAATGAA
TAACAGCCAAAGCTT

FIGURE 6B

C2: SEQ ID NO.: 5

GCATTCAGACCAGCTTGGTCACAGAGAGAGAGTCCATCTCTATAAAAAAATGTTTAAAAATTAGA
CGGGCATGATGGTGCTTGGTGCTTGCCTGTAGTCCCAGCTACTTGGGAGGCTGAGGTGGGAGGAC
TGCCTGAGCCCAGGAACTGGAGATTGCAGGAAGCTATGATCACATCACTGCACTCCAGCCTGGGT
GACAGAGCGAGACTCCGTCTCAAAAAAAAGTCTTTTGTTTTCAGTCATGGTGGTATACGCCTCTA
GTCTCAGCTACTTGGGAGACTGAGGCAGGAGGGTCACTTGAACCCAGGAGTTCGAGTTCAGTCTG
GACAAAATAGCAAGACCCCATCTCTAAATCAAGCAAACAAAGCTT

C7: SEQ ID NO.: 6

CGATTCAGCGCTTGATTCCATTACTGGGTATATACCCAAAATAATATAAATTGTTGGACTATAAT
TATACATGCATGTGTGTGTTCATAACAGCACTATTCATAACAGCAAAGACATGAAATCAACCTAA
ATGCCCATCAAAGGCAGATTGAGCAAAGCAAATATGGTAGATACACACCATGGATGCTATGCAGC
CATAAAAATGAAAAAGATCATGTCCTTTCCAGAAACATGGATGAAGTTGGAGGCCATTATCCTTA
GCAAACTAATGCAGGAACAAAAAACCAAATGCTGCGTGTTCTCACTGATAAGTGGGAGCTAAATG
ATGAGAACAGCAGACACATAGAGGGGACAACAGACACTGGGGTCTACTGGAAGGTGGAGGGTGAG
AGGAGGGAGAGGATCAGGAAAAATAACTAACAGGCACTAGGCTTAATACTTGGGTGACGAAATAA
TCTGTACGACAAACCCCTATGACAAGGGTTTACTTATATAATAAGCTT

E7: SEQ ID NO.: 7

CGATTGCAGAAGCGTCAGGTTTTGTAACCTACGCTTGCAGTTTACTCTCCCCATAGACTTGTAAT
GTTTATCTTTATAATGATAAGGAAAAAACATCACTTTCTGTTATGGCTTTATGCCTATTTTATGT
AGTACAGAATAAACCTAATAAAATGATGTTGGGATTGTTCCATAAGGCATTCTAAAACTTCTTCT
TCCTAGTAGTTGAATTAGAGTTTTTAGTCATTAATAAGCACACATGGCATCATAAAAACACAAAT
CTGAAATAAAAAGAAAGATGTTTTGTCCAGGATTCAGAAAAATATTTTGTCTCCATTTTGCCATA
TGCTTCATGAGATCTTGTACTAAGCTT

E9: SEQ ID NO.: 8

GGGGAATAATTTTGTTATGGGCTAGTGAAAAGTATTTGCTTTCCTAAGGTATGAGCATGTACTGG
TTCACTAACTTCCCAGTTGTTTTCTGGCTGAGAAGAGCTTTTCTTCTGGTGGCACATGTCCATG
ACAGCTGTTTATTCCACATGTTTCCATTGAAAGCATATTAACCTGAGCAAATGGGGATAATTATC
ACAGTGTAAAAATGCCTTTGGATGTTAATGATTCCTCTTCTGTCGTCTCCTTTGATTGGCCTGAC
CCTCGTATTACTATGTATTAATATCCTTAGATCTTCATGGTACCAAGGACATTCCAAAAGTCATC
CACATTGACTTTGGCTCAGAAAGCTT

E12-1: SEQ ID NO.: 9

GGATACTTGCTAGTAGGCTACTGCATTCATTTGGGCTCCACCCCTTTAAGAGGGGCATTAACAAGG
TGAAGTGTATTCCTGGGTCAGTGGCAGCTGGTCTCACTAGCATGTCCCTAGGAGGACAGACAGCA
TAGAAGGGCCCTGGGAACTTGTGCCCTGGGAACTGGGTGCCAGAACTGGGGACGTTTAAAAATAA
CAATCTGGAGCAAATATGATGACTCCTTTTAATTTTTTCAAAGACTGAGATTTGGAAGAGGAGTT
GATCTGTGCTGGGAGACCCTGGCAAACAGTAGGTAGAAGTGACAGGGAGGTGGAGTGGTTAAACT
TTCTAATAATCAATGCTGGTTGACAACAAAATAGACTGCCTCAATTATATTGCATAGAGACCTGC
AGTTGTATTACAACCCTCTTTAGCAAGCCACCAGGAAAATTGGTGCAAAGGAGAAAGATTGCTAT

FIGURE 6C

GGTATGAATCACTCTTTTGGCTGTGTAGATGGGTATGAATGTTTGTCTCTGTCACAGGAAGTATG
GATGCCACCTGGAAGATGACCTATGTGTAGAAGGAAACCCAAGCTT

E12-2: SEQ ID NO.: 10

GCAAGGTATAATACAGTTACGCATAATATGAGATTAGCGGACTTGCACGATTTAAGGTTTTGTTT
TAATTTTAATCACCCAGAGAGCTGCCAGTTGTTCTGATGCCTCTTTGGTTAAGTGAAGCTGAAAA
AAGGGTATAACTCAACTGTCACATGAATTACGGAAGCTT

F6 SEQ ID NO.: 11

GAATTGGGGCATATAATGAAAACAATGGTCGGGAAATGGAAGAGATATATTAACCGAATGGGTCT
GGAAATAAAATAAGTAAAGAACAACTTTATTCCCTGCTCTTTGTGGCTTGTGCAACCTCATGAGA
CAAATGGATGCACCAGGAATCCAGCTGTAATATACAACTGTCAGAGAAACACTTTTAAGCAAAGT
ACAATGTCCTGTGAGAGTACAGTAATGATTAATTTTGATTTGATTAACATTTTGCTTAATAAAT
TTGTTATAGTAAATAAACTAATTTGTTTAGAAAACAGCACCAGTCCTTGTTCAACACATTTCATA
AAGAAGTTCATCCATGGTTTCAATATGCACCCTTGATTATTCTATGGAGAGTTAAATAATAATTT
TATAACTTTGGAGATATTAAGAGGGGGGTTATATATCTCTTCATTCAGTCTCCTATATATTCAGA
CAGAAAAACTGAGGACAAAATAAAGCTT

G12: SEQ ID NO.: 12

ATAAAAGGAAGCAGCTTTAAGGGAAGCAACTTCAATTGAGTGCATTGAGGGCAAAACAGCCAAAG
GGTGATCCTGAATTAGTTTATATGACGTAAAATGCAAAACAGTAAAGCCTGTTATCTAAAGGAAA
AGATAAAAGGCAAAGGCAGAGTCAAAGATAGCAGATTTCAGCAGTCATAGATTTCTCTCTCTGGA
AAGCACAGCTGTTTTTTGTATCTGCCAACCTAATGGAACTCCTCAAATGACTTTTGTTGAAAGCC
CACAGGTCCTGGCAGGGCATACAAGAACTTGAGAACACATGGATTCTTTCTTTCAGGACCTTACA
TTTTAAAAAGGATTCACCATGAGAACTCAATGGAAAACTGATCTGGTGAAGGGGGAAAGACAAGC
TT

H3: SEQ ID NO.: 13

CAAACACAGGGTGATTAAGTTACTCTCTAGAAGAACAAATACCATAGGAGCCCAGACTGGCTTTA
GTGATGATATAAGTAAAGAAAAGCACATTTCAAAAAGCAAAGAAATGACAGTGCTAATTTACTTG
CCCAAATGTTACTGAGAGAACTGTCACTTGAATGTCTCTCAGAAATCATAAGGTGGTGAATGACA
CTCTTTGTCATCAGTATATCCATAGGACAATGATTGTTCTGAAGCAAAATCTTGAATTTCTTACT
CTCTTAACAGGCGGACCTCAGGAAATAATGAATCTTGATAAAAGCATGTAATTTCACACTATTTT
AAATTGAGGTTCTATGTCATTTACTGTGATATATTTCCTGTTGCTCCTTTAAAATGAGTATTTA
CATTAAAATTATTTCACTTAAATGAATAAAACATTAACAACAATAATGCAGCATGCACATTTAAA
TGGAGGATCGACATGATTAGAAGTGCATCTCAAAGGATTTCCCTTTGTTTTCTGATTGTTGCCCC
CTCTGATAGATGATTCATTAATTTCTTGTCACTTGGAGTAAATAGGTGGTTAGAAAGGTCTAGTA
TAAATAAAAATATTTTTCTACTTTGTTTTCATTTTTCAAAATTCTAACAAGCTT

FIGURE 7

Number of amimo acid:
123456789112345678921234567893123456789412345678951234567 89

>A5 [SEQ ID NO.: 14] frameshift -1
FKGQFIIQSHVKEQKGRKKNKADRIVKWVTLFAP = 34

>B9 [SEQ ID NO.: 15] FRAME-1
EFLGTVDIACHSILSVNCILECAGSQLAQGKSLRGLPV = 38

>C2 [SEQ ID NO.: 16] frameshift -1
FKTSLVNRERVHLYKKMFKN = 20

>C7 [SEQ ID NO.: 17] frameshift -1
FHYWVYTQNNINCWTIIIHACVCS = 24

>E7 [SEQ ID NO.: 18] frameshift -1
FSAKVEASGFSVTPTLAVYSPHRLVMFIFIMIRKKHHFLLWLYAYFM = 47

>E9 [SEQ ID NO.: 19] frameshift -1
FFQTLILSMGSVKSICFPKV = 20

>E12 [SEQ ID NO.: 20] frameshift -1
NSTGLSASQATAFHSGLHPFKRGINKVKCIPGSVAAGLTSMSLGGQTA = 48

>F6 [SEQ ID NO.: 21] frameshift -1
FFWGKSKYYIMKTMVGKWKMILFRPELGLEIK = 32

>G12 [SEQ ID NO.: 22] frameshift -1
FMIKELEASYFKGATQIECIEMAKQPKGDPELVYMTVKCKTVKPVI = 46

>H3 [SEQ ID NO.: 23] frameshift -1
FPYMYNHYWVKCELIREFTLLKKVNKYHRSSRIWL = 35

123456789112345678921234567893123456789412345678951234567 89
Number of amimo acid:

GENES AND PROTEINS THAT HOME TO DEVELOPING MICROVESSELS

RELATED APPLICATIONS

This application is a national phase filing under 35 U.S.C. §371 of International Application No. PCT/2007/024629, filed Nov. 30, 2007, which claims the benefit of the filing date of U.S. Provisional application 60/872,210, entitled Novel Genes and Proteins That Home to Developing Microvessels, filed Dec. 1, 2006 and the benefit of the filing date of U.S. Provisional application 60/899,899, entitled Nanoparticle-Based Diagnostics and Therapeutics, filed Feb. 6, 2007. The entire teachings of both of the referenced documents are incorporated by reference herein.

BACKGROUND OF THE INVENTION

Microvasculature development, also called microvessel development, accompanies many conditions and diseases. It would be helpful to have additional information that would make it possible to better understand their role in such conditions and disorders.

SUMMARY OF THE INVENTION

Described herein are polypeptides that home to developing vessels (also referred to as developing vasculature), which include developing microvasculature (also referred to as developing microvessels) and developing collateral vessels (developing collaterals), such as developing microvasculature and developing collateral vessels in mammals, particularly in humans. The polypeptides are referred to herein as developing vessel homing polypeptides, a term that includes the polypeptides themselves and portions thereof, including portions that exhibit substantially the same homing activity as that of the larger homing polypeptide of which they are a portion and portions that are characteristic of a larger homing polypeptide (e.g., an epitope to which an antibody binds specifically). As used herein, the term developing vessel (also referred to as developing vasculature) includes developing microvasculature (also referred to as developing microvessels) and developing collateral vessels (also referred to as developing collaterals). In specific embodiments, the developing vessel homing polypeptides are referred to as developing microvasculature homing polypeptides or developing collateral homing polypeptides. Developing vessel homing polypeptides do not home (to a significant extent) to nondeveloping (pre-existing, stable or not presently expanding) vessels. Developing microvasculature homing polypeptides and developing collateral vessel homing polypeptides do not home (to a significant extent) to nondeveloping or pre-existing (stable, not presently expanding) microvasculature (microvessels) or pre-existing collateral vessels, respectively. Also described is DNA that encodes developing vessel homing polypeptides, such as DNA that encodes developing microvasculature homing polypeptides and DNA that encodes developing collateral vessel homing polypeptides.

Developing vessel homing polypeptides include (a) homing polypeptides that home to only one target (e.g., to developing microvasculature, developing collateral vessels) and do not home to a significant extent to another different target and (b) homing polypeptides that home to more than one target, such as (i) developing microvasculature irrespective of the location, organ or tissue in which it develops (e.g., to developing microvasculature in more than one organ or tissue; to developing microvasculature in vulnerable plaque irrespective of where it develops/in multiple locations); (ii) developing collateral vessels irrespective of the organ or tissue in which they develop (e.g., to developing collateral vessels in more than one location, such as more than one organ or tissue); and (iii) homing polypeptides that home to both developing microvasculature and developing collateral vessels, whether in the same location (same tissue or organ) or irrespective of where they develop/their location (e.g., in more than one organ or tissue).

In specific embodiments, developing vessel homing polypeptides are developing microvasculature homing polypeptides. Developing microvasculature homing polypeptides include developing microvasculature homing polypeptides that home to only one target (e.g., to developing microvasculature in vulnerable plaque) and do not home to a significant extent to another different target (e.g., microvasculature in another location) and homing polypeptides that home to more than one target, such as developing microvasculature irrespective of the location, organ or tissue where it develops/in multiple locations. In one embodiment, developing microvasculature homing polypeptides home to vasa vasorum in vulnerable plaque. These microvessels in an arteriosclerotic plaque are considered to be both a signature element and cause of the "vulnerability" of an arteriosclerotic plaque.

In specific embodiments, developing vessel homing polypeptides are developing collateral vessel (developing collateral) homing polypeptides. Developing collateral vessel homing polypeptides include developing collateral homing polypeptides that home to only one target (e.g., to developing collateral vessel(s) in an ischemic organ or tissue) and do not home to a significant extent to another different target (e.g., developing collateral vessel(s) in another location) and developing collateral vessel homing polypeptides that home to more than one target, such as developing collateral vessel(s) irrespective of the location, organ or tissue where it develops/ in multiple locations. In one embodiment, developing collateral vessel homing polypeptides home to developing collateral vessel(s) in or around the heart or other component of the cardiovascular system.

As described herein, developing vessel homing polypeptides are ligands that can be identified in such a manner that they home to (target) developing vessels in any organ or tissue of interest. In specific embodiments, developing microvasculature homing polypeptides are ligands that can be selected or identified in such a manner that they home to (specifically target) developing microvasculature in any organ or tissue of interest and, in specific embodiments, home to developing microvasculature in vulnerable plaque, which can develop in association with ischemia or prior to development of ischemia; developing microvasculature in the retina, such as occurs in age related macular degeneration (AMD); developing microvasculature associated with tumors, both cancerous and non-cancerous; or newly developing blood vessels (collaterals). In some embodiments, developing vessel homing polypeptides home specifically to developing microvasculature, such as developing microvasculature in vulnerable plaque, which can develop in association with ischemia or prior to development of ischemia; developing microvasculature in the retina, such as occurs in age related macular degeneration (AMD); developing microvasculature associated with tumors, both cancerous and non-cancerous; or newly developing blood vessels (collaterals) and do not home to a significant extent to another different target. Such developing microvasculature homing polypeptides are referred to as specific developing vessel homing polypeptides or specific developing microvasculature homing polypeptides and do not home (to a significant extent) to microvasculature that is stable and not recently developing (expanding). For example, specific developing microvasculature homing polypeptides that home to developing microvasculature in vulnerable plaque do not home (to a significant extent) to developing microvasculature in another tissue or organ or to microvasculature that is stable and not recently developing or expanding.

In specific embodiments, developing collateral homing polypeptides are ligands that can be selected or identified in such a manner that they home to (specifically target) developing collateral vessels in any organ or tissue of interest. In some embodiments, developing vessel homing polypeptides home specifically to developing collateral vessel(s) in one location (e.g. other tissue or organ) and do not home to a significant extent to other tissues or organs.

Also described are uses of developing vessel homing polypeptides, including uses of developing collateral vessel homing polypeptides and uses of developing microvasculature homing polypeptides, such as in methods of diagnosing or aiding in diagnosis of development of collateral vessels and/or microvasculature, including methods of diagnosing or aiding in diagnosis of developing collateral vessels or developing microvasculature in association with ischemia (e.g., in association with stroke or myocardial infarction) or before ischemia develops; developing collateral vessels and/or developing microvasculature in the retina (e.g., in AMD); or collateral vessels and/or microvasculature developing in association with tumors. Developing vessel homing polypeptides, including developing collateral vessel homing polypeptides and developing microvasculature homing polypeptides described herein, are also useful in methods of predicting or aiding in predicting the likelihood that collateral vessels and/or microvasculature will develop in an individual and methods of predicting or aiding in predicting the likelihood that an individual will suffer from a particular condition associated with developing collateral vessels and/or developing microvasculature (e.g., vulnerable plaque and, thus, myocardial infarction and/or stroke). Developing collaterals (developing collateral blood vessels) are, for example, an important compensatory mechanism or response to obstructive arterial disease. Developing collateral vessel homing polypeptides or developing microvasculature homing polypeptides that home to developing collaterals are useful in methods of predicting or aiding in predicting the likelihood that an individual will develop or suffer from obstructive arterial disease.

The disclosure further relates to use of developing vessel homing polypeptides, including developing collateral vessel homing polypeptides and developing microvasculature homing polypeptides and encoding polynucleotides for delivering agents to developing collateral vessels and/or developing microvasculature. In one embodiment, a developing vessel homing polypeptide or an encoding polynucleotide is used to deliver prophylactic or therapeutic drug(s) to developing vessels, in order to prevent or treat a condition associated with developing vasculature and/or to induce formation of collaterals or new vessels that then serve as collaterals. In one embodiment, a developing collateral vessel homing polypeptide or an encoding polynucleotide is used to deliver prophylactic or therapeutic drug(s) to developing collateral vessels, in order to prevent or treat a condition associated with developing collateral vessels or to induce formation of collaterals or new vessels that then serve as collaterals. In a further embodiment, a developing microvasculature homing polypeptide or an encoding polynucleotide is used to deliver prophylactic or therapeutic drug(s) to developing microvessels, in order to prevent or treat a condition associated with developing microvasculature or to induce formation of collaterals or new vessels that then serve as collaterals.

In another embodiment, a developing vessel homing polypeptide, such as a developing collateral vessel polypeptide or a developing microvasculature homing polypeptide or an encoding polynucleotide is used to deliver detection or imaging agents to assess the development of vessels (e.g., development of collateral vessels or microvasculature), such as the extent to which they have developed in an untreated individual or the degree to which they have regressed or stopped developing in a treated individual. In one embodiment, for example, developing collateral vessel or developing microvasculature homing polypeptides are attached or affixed to a biodegradable delivery agents, such as biodegradable nanoparticles, to produce targeting biodegradable delivery agent, such as targeting biodegradable nanoparticles. The targeting biodegradable delivery agents, such as targeting biodegradable nanoparticles, can be designed to target any organ or tissue of the body and, in specific embodiments, to home to developing collateral vessels and/or developing microvasculature, such as developing microvasculature in vulnerable plaque, such as that which develops before ischemia occurs or in association with ischemia; developing collateral vessels or developing microvasculature in the retina, such as occurs in age related macular degeneration (AMD); developing collateral vessels or developing microvasculature associated with tumors, both cancerous and non-cancerous; or newly developing blood vessels (collaterals). Such targeting biodegradable delivery agents, such as targeting biodegradable nanoparticles, or a collection of same, can be used for therapeutic purposes. For example, targeting biodegradable delivery agents, such as targeting biodegradable nanoparticles, carrying a therapeutic agent can be administered to an individual, making it possible to deliver the therapeutic agent to a selected tissue or organ. Using this approach, high levels of therapeutic agent(s) can be delivered to a targeted tissue or organ without the risk of high, potentially toxic, systemic concentrations. For example, therapeutic agents can be delivered, using targeting biodegradable delivery agents, such as targeting biodegradable nanoparticles, to developing collateral vessels or to developing microvasculature in vulnerable plaque, such as that which develops before ischemia or in association with ischemia; developing collateral vessels or developing microvasculature in the retina, such as occurs in age related macular degeneration (AMD); developing collateral vessels or developing microvasculature associated with tumors, both cancerous and non-cancerous; or newly developing blood vessels (collaterals). Such targeting biodegradable delivery agents, such as targeting biodegradable nanoparticles, or a collection of same, can also be used for imaging. For example, targeting biodegradable delivery agents, such as targeting biodegradable nanoparticles carrying an imaging agent, such as gadolinium, that can be imaged by MRI, make noninvasive imaging possible. For example, individuals can be assessed for the presence and/or extent of developing collateral vessels, developing microvasculature and/or vulnerable plaque. For example, individuals shown to have vulnerable plaques (who are at risk of plaque rupture and, thus, acute coronary syndrome or stroke) can be treated earlier and more rigorously than would otherwise be possible. Specific lesions can also be identified using targeting biodegradable delivery vehicles, such as targeting biodegradable nanoparticles.

Also described are compositions, such as pharmaceutical compositions and compositions useful for therapy or prevention of conditions in which developing microvasculature plays a role, and compositions used for detection and/or imaging of developing microvasculature. Such compositions are useful, for example, in treating and detecting conditions such as cardiovascular conditions, ischemia and related conditions, such as myocardial infarction and stroke; retinal conditions, such as AMD; and tumors.

In specific embodiments, developing microvasculature homing polypeptides of the invention are collateral vessel endothelia (CVE) homing polypeptides, which have been shown to home to collateral vessel endothelia and vulnerable plaque endothelia after ischemia. In further embodiments, developing microvasculature homing polypeptides are portions of such CVE homing polypeptides, such as portions that exhibit substantially the same homing activity as the larger CVE homing polypeptide of which they are a portion and portions that are characteristic of a larger CVE homing polypeptide. DNA that encodes the CVE homing polypeptides is also described herein. As described herein, Applicants hypothesized that there are specific protein fragments coded for by the human genome that carry the signature for homing to particular surface molecules that are specifically exposed in distinct regions of the healthy or the diseased vasculature in humans. Further, they hypothesized that these signature proteins are carried by cells, such as stem cells, precursor cells and/or mature cells, in human bone marrow. As described herein, Applicants have identified signature polypeptides that home to collateral vessels (developing blood vessels), particularly endothelia of these developing blood vessels, after ischemia. This has been accomplished by panning a phage display library carrying fragments of expressed proteins from human bone marrow. The collateral vessel endothelia (CVE) homing polypeptides are ligands of tissue-specific receptors, particularly ligands of collateral vessel endothelia and, thus, are polypeptides that target collateral vessel endothelia.

Thus, the present invention relates, in specific embodiments, to CVE homing polypeptides and nucleic acids encoding CVE homing polypeptides, which are useful, for example, for diagnostic and therapeutic purposes, particularly diagnosis and therapy of individuals in whom collateral vessels are developing or have developed, such as those associated with ischemia, as well as for purposes of predicting the likelihood or risk that an individual will develop collateral vessels. Such homing polypeptides and nucleic acids are also useful for diagnosis and therapy of individuals in whom plaque rupture or acute ischemia has occurred and individuals who are at risk of ischemia or plaque rupture, which leads to cardiovascular event(s), such as acute coronary syndrome or stroke. It further relates to CVE homing polypeptides and nucleic acids encoding CVE homing polypeptides, both of which are useful for predicting the likelihood or risk that an individual will develop plaque rupture (will experience rupture of vulnerable plaque) or acute ischemia. The CVE homing polypeptides and nucleic acids encoding them are useful for diagnosis and therapy of developing and established collateral vessels, vulnerable plaque endothelia, developing and ruptured vulnerable plaque, and acutely ischemic myocardium.

Further described herein are uses of CVE homing polypeptides, such as in methods of diagnosing or aiding in diagnosis of collateral vessel formation, methods of predicting the likelihood that collateral vessels will develop in an individual; methods of diagnosing or aiding in the diagnosis of development of vulnerable plaque in an individual; methods of predicting or aiding in predicting the likelihood that an individual will experience disruptions of vulnerable atheromatous plaque; methods of predicting or aiding in predicting the risk an individual will experience acute coronary syndrome; methods of predicting survival or aiding in predicting survival of an individual in whom vulnerable atheromatous plaque has developed; predicting or aiding in predicting how long it will be until an individual with vulnerable plaque will experience plaque rupture; methods of assessing the effectiveness of therapy; and methods of assessing the stage or progression of atheromatous plaque vulnerability (e.g., its fragility) in an individual.

Also described herein is the use of CVE homing polypeptides and the encoding polynucleotides for delivering agents, such as prophylactic or therapeutic drugs and detection or imaging agents, to collateral vessels, particularly collateral vessel endothelial cells, and to vulnerable plaque; compositions, such as pharmaceutical compositions and compositions useful for detection and/or imaging of collateral vessels and vulnerable plaque, which comprise a (at least one) CVE homing polypeptide or fragment thereof or an (at least one) polynucleotide that encodes a CVE homing polypeptide and antibodies that specifically bind CVE homing gene products or portions thereof, such as antibodies that specifically bind homing domains of CVE homing polypeptides.

Specific embodiments relate to CVE homing polypeptides, including polypeptide fragments that are homing domains, encoded by DNA whose sequences are presented herein or fragments thereof; methods in which one or more of the CVE homing polypeptides or fragments thereof are used; methods in which one or more of the DNA encoding CVE homing polypeptide is used; compositions comprising one or more of the CVE homing polypeptide encoding polynucleotides or a portion(s) thereof; compositions comprising (a) a CVE homing polypeptide and (b) an agent to be targeted to collateral vessels (e.g., collateral vessel endothelia) and/or vulnerable plaque in an individual; and antibodies that specifically bind (recognize) products (proteins, polypeptides) that are encoded by DNA whose sequences is provided herein or portions of any of the DNA.

In specific embodiments, compositions are pharmaceutical compositions that comprise (a) one or more CVE homing polypeptides or portions thereof (e.g., one or more of the CVE homing polypeptides encoded by any one of the DNAs represented by SEQ ID NOs 1-13) or one or more DNA encoding a CVE homing polypeptide, such as DNA encoding one or more CVE homing polypeptide (e.g., one or more DNA of SEQ ID NOs 1-13, each of which encodes a CVE homing polypeptide) or one or more of CVE homing polypeptides of SEQ ID NOs 14-23, and (b) a therapeutic agent (a drug) to be delivered to developing collateral vessels, developing microvasculature and/or vulnerable plaque. Therapeutic agents that can be included in a pharmaceutical composition of the present invention include those that enhance collateral development (e.g., a growth factor) or decrease microvasculature, such as radioisotopes and chemotherapeutic drugs, that would favorably influence vulnerable plaque or modify the extent to which it occurs in an individual.

A pharmaceutical can include a pharmaceutically acceptable carrier, which is a compound suitable for administration to individuals, such as humans. The pharmaceutical compositions can contain other components useful in formulating pharmaceutical preparations for administration to subjects, preferably humans, including surfactants, solvents, preservatives, diluents, buffering agents and the like, all of which are standard in the pharmaceutical arts.

Suitable surfactants for use with the present invention include nonionic agents, such as long-chain fatty acids and their water-insoluble derivatives. These include fatty amines such as lauryl acetyl and stearyl amine, glyceryl esters such as the naturally occurring mono-, di- and triglycerides, and fatty acid esters of fatty amines, such as propylene glycol, polyethylene glycol, sorbitan, sucrose and cholesterol. Also useful are compounds that have polyoxyethylene groups added through an ether linkage with an amine group. Compounds that are also useful in the present invention include the polyoxyethylene sorbitan fatty acid esters and polyoxyethylene glycerol and steroidal esters. Some of the preferred surfactants are Cremophor® EL and Cremophor® EL-P, which are polyoxyethylated castor oil surfactants.

It is contemplated that other surfactants may be used to solubilize the compositions described herein. For example, it is contemplated that polysorbate 80, polysorbate 20, sodium laurate, sodium oleate, and sorbitan monooleate may be useful in certain embodiments of the present invention. Anionic surfactants may also be useful in the practice of the present invention. Examples of these include, but are not limited to, sodium cholate, sodium lauryl sulfate, sodium deoxycholate, sodium laurate, sodium oleate, and potassium laurate.

In certain embodiments, dehydrated ethanol may be used as a solvent for the compositions described herein. In other embodiments, glycols such as propylene glycol or polyethylene glycol are within the scope of the invention. Simple complex polyols may also be suitable solvents. Moreover, the use of non-dehydrated amines may also be suitable within the scope of the present invention.

Suitable buffering agents include: acetic acid and a salt (1-2% W/V); citric acid and a salt (1-3% W/V); and phosphoric acid and a salt (0.8-2% W/V).

Suitable preservatives include antimicrobial agents, such as, benzalkonium chloride (0.003-0.03% W/V); chlorobutanol (0.3-0.9% W/V); parabens (0.01-0.25% W/V) and thimerosal (0.004-0.02% W/V) and/or suitable antiantioxidants, such as, ascorbic acid, ascorbyl pamitate, BHA, BHT, hypophosphorous acid, monothioglycerol, potassium metabisulfite, propyl gallate, sodium formaldehyde sulfoxylate, sodium metabisulfite, sodium bisulfite, sodium thiosulfate, sulfur dioxide, tocopherol and/or tocopherols excipient.

In one aspect, the pharmaceutical compositions comprise a developing microvessel homing polypeptide or a developing collateral vessel polypeptide and one or more therapeutic agents. The therapeutic agent can be an agent that enhances collateral development, such as a growth factor or an angiogenic factor or an agent that decreases microvasculature, such as radioisotopes and chemotherapeutic agents.

In further specific embodiments, the compositions of the present invention are useful for detection and/or imaging of collateral vessels and vulnerable plaque. In some embodiments, the developing vessel homing polypeptides or encoding DNA are bound to a label which can be a fluorescent label, an enzyme label, an enzyme substrate label, a radioactive label, a nuclear magnetic resonance active label, a luminescent label or a chromophore label. In some embodiments, the developing vessel homing polypeptides are bound to a radioisotope. Some radioisotopes could emit α radiations. Others could emit β radiations. Other radioisotopes could emit γ radiations. Examples of radioisotopes that may be used in this invention include but are not limited to $^{225}$Ac, $^{211}$At, $^{212}$Bi, $^{213}$Bi, $^{186}$Rh, $^{188}$Rh, $^{177}$Lu, $^{90}$Y, $^{131}$I or $^{67}$Cu, $^{125}$I, $^{123}$I or $^{77}$Br.

Provided herein are compositions and methods for determining the presence of and/or the presence of elevated levels of one or more of the CVE homing polypeptides described herein, or polynucleotides encoding them, in a sample from an individual at risk for or subject to developing a condition associated with or characterized by poor development of microvasculature or collateral vessels, pathologic development of microvessels, such as in the eye, with resulting diseases (e.g. macular degeneration) or in a sample from an individual at risk for or subject to developing vulnerable plaque. In a method of this type, levels of at least one CVE homing polypeptides or at least one polynucleotide encoding such CVE homing polypeptides distinct from levels evident in controls is correlated, for example, with increased risk of poor development of collateral vessels or pathologic development of microvessels, such as in the eye, with resulting diseases.

Also provided herein are methods for determining survival rates (e.g., the probability of survival) or the recurrence of coronary artery or other vascular disease in an individual, such as an individual diagnosed as suffering from coronary artery or other vascular disease, comprising: 1) assessing the presence of and/or measuring the levels of one or more of the following: a) a polynucleotide disclosed herein in FIG. 6A-6C (SEQ ID NOs 1-13), a complement thereof or the corresponding mRNA; b) a polypeptide encoded by any one of the polynucleotides disclosed in FIG. 6A-6C (SEQ ID NO. 1-13) or a polypeptide disclosed in FIG. 7 (SEQ ID NO. 14-23) or a portion of such a polypeptide; or c) a polynucleotide that, through the degeneracy of the genetic code encodes a polypeptide having the same or substantially the same amino acid sequence and homing ability as a CVE homing polypeptide encoded by any one of the polynucleotides of SEQ ID NOs. 1-13 and 2) comparing the results of 1) with results obtained in a control, wherein the presence of or presence of levels distinct from that of a control is indicative of a difference in survival rate. In some instances, a lower level in a sample from an individual being assessed of the component(s) being measured (polynucleotide or polypeptide) is indicative of a decrease in survival rate. In other instances, a higher level or the presence in a sample from an individual being assessed of the component(s) being measured is indicative of a decrease in survival rate. encoding them. In some instances, the presence of or the presence of elevated levels of the component(s) being measured is indicative of an increase in survival rate. Alternatively, the presence of or the presence of elevated levels of the component(s) being measure is indicative of a decrease in survival rate. A variety of samples (e.g., blood, serum, vessel, organ or tissue such as heart tissue) can be assessed using this method of determining survival rate.

Also provided herein are compositions comprising such CVE homing polypeptides and/or portions thereof and compositions comprising polynucleotides that encode CVE homing polypeptides or portions thereof, as well as kits comprising such polypeptides and polynucleotides.

Antibodies that specifically recognize (bind to) a CVE homing polypeptide or portion of a CVE homing polypeptide are also described. They can be monoclonal or polyclonal and can be produced using the information provided herein and art recognized methods. One or more such antibodies can be used in diagnostic methods and in therapeutic methods.

In certain embodiments, the present invention provides a method of targeting an agent to vulnerable plaque in an individual, comprising administering to an individual in need thereof an effective amount of a composition comprising a developing microvasculature homing polypeptide that homes to vulnerable plaque and the agent to be targeted to vulnerable plaque in the individual, whereby the agent is targeted to the vulnerable plaque. For example, the agent to be targeted to vulnerable plaque is a therapeutic drug or a detection/imaging agent (e.g., radioisotopes, dyes, fluorescent molecules, and pigments).

According to another aspect of the invention, a developing vessel homing polypeptide that homes to a developing vessel is provided. The developing vessel may be a developing microvessel or developing collateral vessel. In some embodiments, the developing vessel homing polypeptide is attached to a biodegradable delivery agent.

According to another aspect of the invention, a polynucleotide encoding a developing vessel homing polypeptide is provided. The developing vessel homing polypeptide is selected from the group consisting of: SEQ ID NO 1; SEQ ID NO 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10; SEQ ID NO 11; SEQ ID NO 12; SEQ ID NO 13 and a sequence that, due to the degeneracy of the genetic code, encodes the same polypeptide as a polypeptide encoded by any one of SEQ ID NOs 1-13, complements thereof and nucleic acids that hybridize under stringent conditions to the polynucleotides.

According to another aspect of the invention, an antibody, or a fragment thereof, that specifically binds a developing vessel homing polypeptide.

In one aspect of the invention, an antibody, or a fragment thereof, that specifically binds a developing vessel homing polypeptide is provided. The developing vessel homing polypeptide is selected from the group consisting of: SEQ ID NO 14; SEQ ID NO 15; SEQ ID NO 16; SEQ ID NO 17; SEQ ID NO 18; SEQ ID NO 19; SEQ ID NO 20; SEQ ID NO 21; SEQ ID NO 22; or SEQ ID NO 23.

According to another aspect of the invention, a polynucleotide encoding a developing vessel homing polypeptide is provided. The developing vessel homing polypeptide is selected from the group consisting of: SEQ ID NO 1; SEQ ID NO 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10; SEQ ID NO 11; SEQ ID NO 12; SEQ ID NO 13 and a sequence that, due to the degeneracy of the genetic code, encodes the same polypeptide as a polypeptide encoded by any one of SEQ ID NOs 1-13.

The antibody may be a monoclonal antibody, a polyclonal antibody, a chimeric antibody, a bispecific antibody, a heteroconjugate antibody, or a single chain (ScFv) antibody. The antibody may be coupled to a therapeutic moiety. The therapeutic moiety may be ricin, a radioisotope, a clotting agent, a thrombolytic factor, a chemotherapeutic agent, a radiosensitizing agent, an anti-angiogenesis agent, an anti-motility agent or an immunomodulatory agent.

In some embodiments, the antibody is coupled to a radiologic or other imaging molecule. Examples of radiologic or other imaging molecule include but are not limited to a radioisotope, a dye, a pigment and a fluorescent molecule (such as luciferase, and fluorescein).

According to another aspect of the invention, a method for determining the risk of a condition or disorder associated with or characterized by at least one developing vessel homing polypeptide in an individual. The method comprises determining the presence of at least one developing vessel homing polypeptide or at least one polynucleotide encoding a developing vessel homing polypeptide in a sample from an individual at risk for developing a condition associated with or characterized by developing vessel. The presence of or the presence of elevated levels of at least one developing vessel homing polypeptide or at least one polynucleotide encoding a developing vessel homing polypeptide, is correlated with increased risk of a condition or disorder associated with or characterized by developing vessel homing polypeptides.

According to another aspect of the invention, a method of targeting an agent to developing microvasculature in an individual is provided. The method comprises administering to the individual in need thereof an effective amount of a composition comprising a developing vessel homing polypeptide that homes to developing vessel and the agent to be targeted to developing vessel, whereby the agent is targeted to developing vessel.

According to another aspect of the invention, a method of treating a condition or disorder associated with or characterized by at least one developing vessel homing polypeptide in an individual is provided. The method comprises, administering to a subject in need of such treatment a developing vessel homing polypeptide linked to a therapeutic agent in an amount effective to treat the condition, or an effective amount of a composition that inhibits the condition.

According to another aspect of the invention, a pharmaceutical composition is provided. The pharmaceutical composition comprises one or more developing vessel homing polypeptides of the invention, or a portion thereof, a therapeutic agent, and a pharmaceutically acceptable carrier. In some embodiments, the therapeutic agent enhances collateral development or decreases developing vessel development.

According to yet another aspect of the invention, a kit comprising one or more homing polypeptides or portions thereof of the invention is provided.

According to another aspect of the invention, a method for identifying the presence of a developing vessel in an individual is provided. The method comprises administering to the individual one or more developing vessel homing polypeptides and detecting the homing of the developing vessel homing polypeptides. An increased homing activity indicates that the individual has a developing vessel.

According to still another aspect of the invention, a method for identifying the presence of a developing vessel in a sample form an individual is provided. The method comprises exposing the sample to one or more developing vessel homing polypeptides and detecting the homing of the developing vessel homing polypeptides. An increased homing indicates that the sample contains a developing vessel.

According to still another aspect of the invention, a method for identifying an individual as having a developing vessel is provided. The method comprises detecting the presence of a developing vessel homing polypeptide in the individual. The presence of the developing vessel homing polypeptide in the subject indicates the subject has a developing vessel.

According to still another aspect of the invention, a method for identifying the presence of a developing vessel in a sample from an individual is provided. The method comprises detecting the presence of a developing vessel homing polypeptide in the sample wherein the presence of the developing vessel homing polypeptide in the sample indicates the presence of a developing vessel in the sample.

The following embodiments apply equally to the various aspects of the invention set forth herein unless indicated otherwise.

The developing vessel homing polypeptide is selected from the group consisting of: SEQ ID NO 1; SEQ ID NO 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10; SEQ ID NO 11; SEQ ID NO 12; SEQ ID NO 13 and a sequence that, due to the degeneracy of the genetic code, encodes the same polypeptide as a polypeptide encoded by any one of SEQ ID NOs 1-13.

The developing vessel homing polypeptide may be any one of: SEQ ID NO 14; SEQ ID NO 15; SEQ ID NO 16; SEQ ID NO 17; SEQ ID NO 18; SEQ ID NO 19; SEQ ID NO 20; SEQ ID NO 21; SEQ ID NO 22; SEQ ID NO 23, or a fragment thereof.

In some embodiments developing vessel homing polypeptide homes specifically to developing microvasculature in vulnerable plaque. In some embodiments developing vessel homing polypeptide homes specifically to developing microvasculature in the retina, such as occurs in age related macular degeneration (AMD). In some embodiments developing vessel homing polypeptide homes specifically to developing microvasculature associated with a tumor, cancerous or non-cancerous. In some embodiments developing vessel homing polypeptide homes specifically to a developing collateral blood vessel.

In some embodiments, the antibody, or a fragment thereof, specifically binds developing vessel homing polypeptide(s) encoded by a polynucleotide selected from the group consisting of: SEQ ID NO 1; SEQ ID NO 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10; SEQ ID NO 11; SEQ ID NO 12; SEQ ID NO 13 and a sequence that, due to the degeneracy of the genetic code, encodes the same polypeptide as a polypeptide encoded by any one of SEQ ID NOs 1-13.

BRIEF DESCRIPTION OF THE DRAWINGS

FIG. 6A-6C lists the phage insert sequences, designated A5, A12, B9, C1, C2, C7, E7, E9, E12-1, E12-2, F6, G12 and H3 (SEQ ID NOs: 1-13, respectively). See also the Table Summary of Found Sequences. Table 1.

FIG. 7 lists the sequences of fusion proteins with gene 10 identified by mass spectrometry of T7 phage expressing the different collateral homing sequences A5, B9, C2, C7, E7, E9, E12, F6, G12 and H3 (SEQ ID NOs: 14-23, respectively) produced in E. Coli. Without frame shift, only very short peptides (<6 amino acids) were typically produced.

DETAILED DESCRIPTION OF THE INVENTION

Figure 1:
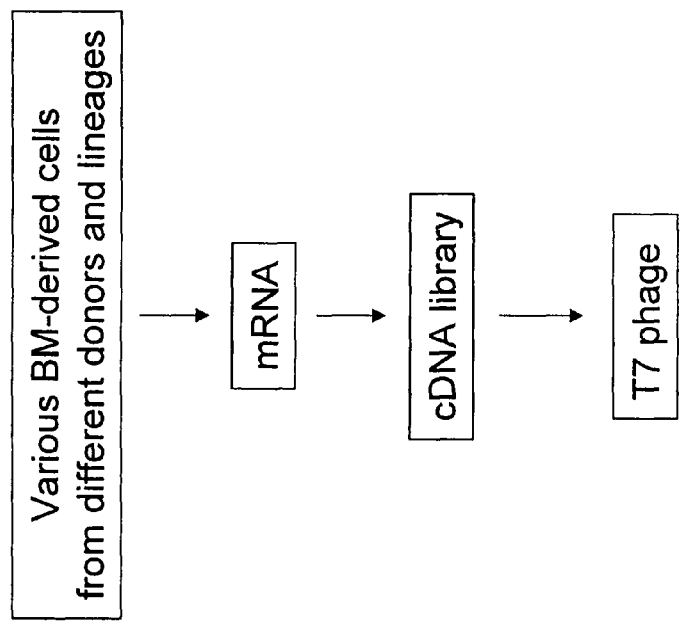
FIG. 1 depicts a flow chart describing the general concept of library generation. The cell sources were bone marrow matrix-bound cells (stem and progenitor cells not released into the circulation) and differentiated cells, derived from different donors. Cells were stimulated by attachment and with growth factors. Cellular mRNA was isolated and cDNA was generated to form a cDNA library. The library was inserted into T7 phage as a vector.

As described herein, Applicants have identified polypeptides that specifically target or home to developing microvasculature. Such developing microvasculature homing polypeptides are ligands that home to (target) any organ or tissue of the body and are useful to deliver compounds and molecules to the target or tissue to which they home. In doing so, Applicants used a human bone marrow cDNA phage display library that displays expressed genes from stem cells and precursor and mature monocytes and a biopanning technique. In a specific embodiment, Applicants used such a phage display library and a method in which the phage display library is biopanned to the ischemic hind limb model and identified polypeptides, referred to herein as developing vessel homing polypeptides (e.g., developing collateral vessel homing polypeptides), that home to endothelial cells of collateral vessels. The insert sizes of cDNAs in the phage display library were between 100 and 2,000 nucleotides, with the majority between 300 and 900 nucleotides. The methods used in this embodiment are described in detail in the figures and their legends, as well as in the example.

Described herein are polypeptides that target or home to developing microvasculature; nucleic acids (DNA, RNA) that encode the polypeptides; methods in which the polypeptides and encoding nucleic acids are used; compositions that comprise one or more of the polypeptides and/or one or more of the encoding nucleic acids; antibodies that bind to polypeptides that specifically target or home to developing microvasculature; and kits that contain one or more of the polypeptides, one or more of the encoding nucleic acids and/or one of more antibodies that bind to polypeptides that specifically target or home to developing microvasculature. In specific embodiments, polypeptides are developing collateral vessel homing polypeptides or developing microvasculature homing polypeptides or polypeptides that home to developing microvasculature, such as in vulnerable plaque, such as that which develops before or in association with ischemia; developing collateral vessels or developing microvasculature in the retina, such as occurs in age related macular degeneration (AMD); developing collateral vessels or developing microvasculature associated with tumors, both cancerous and non-cancerous; or newly developing blood vessels (collaterals).

Also provided herein are compositions and methods for determining the status of an individual or the risk that an individual has or will develop a condition in which developing microvasculature (such as poor development of collaterals or pathologic development of microvessels) plays a role or is indicative of a condition of interest or concern (e.g., vulnerable plaque, ischemia (e.g., in association with stroke or myocardial infarction), AMD; tumors). Developing collateral vessel homing polypeptides and developing microvasculature homing polypeptides of the present invention are also useful in methods of predicting the likelihood that collateral vessels or microvasculature will develop in an individual and methods of predicting or aiding in predicting the likelihood that an individual will develop a particular condition associated with developing collateral vessels or developing microvasculature (e.g., vulnerable plaque and, thus, myocardial infarction and/or stroke).

The present invention discloses the preparation of libraries that can be utilized for the identification of homing genes. In particular, described herein is the preparation of a human bone marrow cDNA phage display library that displays expressed genes from stem cells and precursor and mature monocytes and has been shown to be useful in identifying polypeptides that home to developing microvasculature. In a specific embodiment, the library is used with an appropriate model (an ischemic hind limb model) to identify polypeptides that home to collateral vessel endothelia after ischemia. Such a library can be used in combination with a different model in order to identify polypeptides that home to developing collaterals or developing microvasculature associated with other conditions. The model is preferably a mammal, such as, for example, a human, a mouse or a rabbit, but may also be any other mammal. Alternatively, the method may utilize any animal, including non-mammals, that allows for the injection of phage library and demonstrates a significant response.

Disclosed herein are polynucleotides that were identified by methods as disclosed herein, including the method comprising: (a) administering a phage displaying library comprising a collection of phages containing polynucleotides from human bone marrow to an individual, such as an appropriate animal model; (b) selecting phage that localize in a target organ or tissue (e.g., developing collateral vessels or developing microvasculature); (c) collecting phage from the selected organ or tissue; (d) repeating steps (a) and (c) for one or more cycles; and (e) identifying one or more polynucleotides encoding a polypeptide, or fragment thereof, from selected phage that home to or target a tissue(s) of interest, such as tissues in an ischemic hind limb animal model. Such polynucleotides include the polynucleotides of SEQ ID NOs. 1-13, shown in FIG. 6A-6C and complements thereof. Such polypeptides include the polypeptides of SEQ ID NOs 14-23, shown in FIG. 7 and fragments thereof.

Many types of phage may be used to create the library. Preferably, the phage used in the creation of the library has one or more of the following characteristics: the ability to contain and express relatively large polynucleotides, such as, for example, between about 300-3000 nucleotides and/or expresses the clone from the library at a low copy number, such as, for example, between about 0.1 copy to about 1 copy per phage. Such phages are commercially available (e.g., a T7Select vector using T7Select 1-1 phage). By way of example, a phage display library may comprise and express polynucleotides isolated from a primary tumor, such as, for example, colon cancer or from a cell line such as, for example, a colon cancer cell line (e.g., LSl74T; American tissue culture collection, ATCC, Rockville, Md.). Preferably, the phage themselves (phage without a recombinant insert) have a low relative retention to target organs or cells. Retention, which may relate to direct binding, non-specific association, or active uptake, will cause phage to nonspecifically associate with target cells. By identifying and selecting only phage with low retentions by target cells, the highest selectivity can be achieved.

The library is administered to any subject, such as a mouse or other mammal. The animal may be a normal animal or an animal model of disease. Alternatively, the library may be contacted with in vitro systems or models. In an animal, such as a mouse, a volume of between about 3 microliters to about 100 microliters, 5 microliters to about 100 microliters, 10 microliters to about 100 microliters or other appropriate volume containing between about $10^7$ to about $10^{10}$ phage is administered. A volume sufficient to produce desanguination in the method used can be used. Phage, based on the expression product displayed, target to selected organs, tissues or other areas of the body. Accordingly, the library is administered and allowed to circulate for a time sufficient to allow binding to the target tissue and/or organ of the binding domains expressed in the library. The optimal circulation time will vary with the size/weight of the animal, volume and/or complexity of the library. By way of example, for a mouse circulation time may be between about one minute to about ten minutes.

After sufficient circulation time, the animal is euthanized and the target organs collected for analysis. The method described herein may be further enhanced by further comprising perfusing the anesthetized animal with an isotonic solution, such as an isotonic salt solution, with or without proteins (e.g., BSA) to minimize non-specific binding of phage. Examples of isotonic salt solutions include, but are not limited to, phosphate buffer. Perfusion is continued, preferably until desanguination (e.g., little or no blood exits the vena cava, organs appear white in color.) By way of example, volumes of between about 1 to about 100, such as about 3, 5, 10, 15 or 20 times the volume of the animal may be used.

Any organ or tissue may be harvested for analysis. By way of example, these include, but are not limited to, bone marrow, lung, skin, liver and/or brain. Generally the tissue or organ harvested will be selected based on the origin of the library. By way of example, metastasis in colon cancer is often to the liver, marrow, lung and/or bone marrow. If the library used in the method comprises polynucleotides from a primary colon cancer tumor or cell line, liver lung and/or bone marrow can be harvested. Phage are collected from the selected tissues and/or organs, amplified, if necessary, and injected into another animal. Through successive rounds of injection, selection, and amplification, a collection of phage can be isolated that are specific for the selection criteria. By way of example, between about two to about five rounds of injection, selection, and amplification may performed. These collections can be further selected or the polynucleotides from individual or groups of phage isolated and identified. Polynucleotides identified by these methods can be used for both diagnostic and therapeutic purposes.

The method described herein for identifying targeting polypeptides that home to collateral vessel endothelia is also useful for identifying polypeptides that home to developing microvasculature in other tissues and/or in other conditions or diseases. By way of example, such diseases or disorders may include, but are not limited to, arteriosclerosis, coronary artery disease, stroke, diabetic vascular damage (e.g., kidney vascular damage) or retinopathy. Examples of animals models to be used in the methods described herein include, but are not limited to, cardiovascular diseases in pig, rat, rabbit arterial stenosis and vascularization.

Polynucleotides

Provided herein are polynucleotides identified by the method described herein. Such polynucleotides include the polynucleotides whose sequences are presented in FIG. 6A-6C, fragments thereof, and complements thereof. The term polynucleotide is used broadly and refers to polymeric nucleotides of any length (e.g., oligonucleotides, genes, small inhibiting RNA etc). The polynucleotide may be, for example, linear, circular, supercoiled, single stranded, double stranded or branched. It is, however, understood by one skilled in the art that due to the degeneracy of the genetic code, variations in the polynucleotide sequences shown will result in a polynucleotide sequence capable of encoding a polypeptide as disclosed herein in FIGS. 6A-6C it is understood that the polynucleotide sequences disclosed herein can encode a polypeptide of all three possible reading frames. The polypeptides encoded by the polynucleotides disclosed herein include all frame shifted variants. Such polynucleotide sequences are intended to be encompassed within the present invention. Further, a person of skill in the art will understand that there are naturally occurring allelic variations of the polynucleotide sequences shown herein. These variations are also intended to be encompassed by the present invention.

Provided herein are methods that comprise the use of one or more polynucleotides that comprise the polynucleotide sequence encoding polypeptides of any one of SEQ ID NOs. 1-13, shown in FIG. 6A-6C.

Polynucleotides that hybridize under stringent conditions to a polynucleotide that encodes a polypeptide of any one of SEQ ID NOS. 1-13 can also be used in the methods disclosed herein. Hybridization reactions can be performed under conditions of different stringency. Conditions that increase stringency of a hybridization reaction are widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 4×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. In a preferred embodiment hybridization and wash conditions are done at high stringency. By way of example hybridization may be performed at 50% formamide and 4×SSC followed by washes of 2×SSC/formamide at 50° C. and with 1×SSC.

Polypeptides

The term polypeptide is used broadly herein to include peptide or protein or fragments thereof. Also intended to be encompassed are peptidomimetics, which include chemically modified peptides, peptide-like molecules containing normaturally occurring amino acids, peptoids and the like, have the selective binding of the targeting domains provided herein. ("Burger's Medicinal Chemistry and Drug Discovery" 5th ed., vols. I to III (ed. M. E. Wolff; Wiley Interscience 1995).

In some examples of the methods, the polypeptide comprises the amino acid sequence encoding by any one of SEQ ID NOs. 1-13 (FIG. 6A-6C), or the amino acid sequence of anyone of SEQ ID NOs. 14-23 (FIG. 7). This invention further includes polypeptides or analogs thereof having substantially the same function as the polypeptides of this invention. Such polypeptides include, but are not limited to, a substitution, addition or deletion mutant of the polypeptide. This invention also encompasses proteins or peptides that are substantially homologous to the polypeptides.

Methods of Prognosis and/or Diagnosis

Provided herein are methods for determining the presence of developing microvasculature homing polypeptides or polynucleotides encoding them, in a sample from an individual at risk for developing a condition associated with or characterized by developing microvasculature, wherein the presence of, or presence of elevated levels of, a developing microvasculature homing polypeptide(s), or polynucleotides encoding them, is correlated with increased risk of a condition or disorder associated with, or characterized by, developing microvasculature homing polypeptides. In some examples, the presence of cumulative elevated levels of one or more CVE homing polypeptides, such as those encoded by polynucleotide of SEQ ID NOs 1-13, or polypeptides having the amino acid sequence of SEQ ID NOs 14-23, (relative to a control) are correlated with an increased risk of ischemia.

Also provided herein are methods for determining the risk of a condition or disorder associated with or characterized by developing microvasculature homing polypeptides in an individual, such as cardiovascular conditions, ischemia and related conditions, such as myocardial infarction and stroke; retinal conditions, such as AMD; and tumors. Such methods comprise detecting the presence of and/or measuring the levels of one or more of the polypeptides such as those encoded by the nucleotides of SEQ ID NOs 1-13, or polypeptides having the amino acid sequence of SEQ ID NOs. 14-23 in a sample from the individual, wherein the presence and/or presence of elevated levels of one or more of the polypeptides or polynucleotides encoding them is correlated with an increased risk of developing the condition.

The methods provided herein maybe prognostic (e.g., detect subclinical conditions, detection of subclinical metastasis in at risk patients, risk of developing a condition associated with or characterized by developing microvasculature homing polypeptides) or diagnostic (e.g., detect the condition, monitor disease progression or treatment). One embodiment provides methods of prognosing and/or diagnosing metastatic disease in a subject. In one embodiment, the method comprises detecting the level of a polynucleotide encoding a developing microvasculature homing polypeptide in a sample obtained from a subject, wherein a level of the polynucleotide that is abnormal (e.g., higher or lower) relative to a control sample is indicative of the condition. In another embodiment, the method comprises detecting the presence or absence of a polynucleotide encoding a developing microvasculature homing polypeptide in a sample obtained from the subject, wherein the presence of the polynucleotide is indicative of the associated condition. Conventional methodology may be used to detect the polynucleotides in the method described herein. Examples include, but are not limited to, PCR analysis, RT-PCR, Northern analysis or microarrays as described herein below. Examples of a sample obtained from a subject include, but is not limited to, blood, biopsy sample, pathology sample, urine or cerebrospinal fluid.

Yet another aspect of this invention provides methods of prognosing, imaging and/or diagnosing a condition associated with or characterized by developing microvasculature homing polypeptide(s) in a subject. In one embodiment, the method comprises detecting the level of such a polypeptide(s) in a sample obtained from a subject, wherein a higher level of the polypeptide relative to a control sample is indicative of the condition. In another embodiment, the method comprises detecting the presence or absence of a developing microvasculature homing polypeptide(s) in a sample obtained from the subject, wherein the presence of the polypeptide is indicative of the condition. Conventional methodology may be used to detect the polypeptides in the method described herein.

Examples include, but are not limited to, Western blot analysis or protein microarrays. Other methods of quantitative analysis of proteins include, for example, proteomics technologies such as isotope coded affinity tag reagents, MALDI TOF/TOF tandem mass spectrometry, and 2D-gel/mass spectrometry technologies. These technologies are commercially available from, for example, Large Scale Proteomics, Inc. (Germantown, Md.) and Oxford Glycosystems (Oxford UK). Methods for quantitatively measuring proteins such as ELISA analyses are well known. Kits for measuring levels of many proteins using ELISA assays are commercially available from many suppliers. In addition, methods for developing ELISA assays in the laboratory are well known. See for example Antibodies: A Laboratory Manual (Harlow and Lane Eds. Cold Spring Harbor Press). Antibodies for use in such ELISA methods either are commercially available or are prepared using well-known methods. Examples of a sample obtained from a subject include, but is not limited to, blood, biopsy sample, pathology sample, urine or cerebrospinal fluid.

Antibodies

The invention also provides antibodies, or fragments thereof, that specifically bind developing microvasculature homing polypeptide(s) for use in the methods disclosed herein, or which specifically bind one or more of the polypeptides disclosed herein in FIG. 7 (SEQ ID NOs 14-23), or which are encoded by the polynucleotides of FIG. 6A-6C (SEQ ID NOs 1-13). The antibodies can be monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv) antibodies, mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). The epitope(s) can be continuous or discontinuous. The antibodies may be made by any method known in the art and tested by the method described herein. In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733, 743; 6,265,150; and Winter et al., Annu. Rev. Immunol. 12:433-455 (1994). Alternatively, the phage display technology (McCafferty et al., Nature 348:552-553 (1990)) can be used to produce human antibodies and antibody fragments in vitro, from immunoglobulin variable (V) domain gene repertoires from unimmunized donors.

Yet another aspect of the invention relates to detection of a condition associated with, or characterized by, developing microvasculature homing polypeptide(s) in a subject, such as a human, utilizing one or more antibodies described herein, such as antibodies to any of the polypeptides, SEQ ID NOs 14-23, or encoded by the polynucleotides of SEQ ID NOs 1-13, or fragments thereof, or epitopes thereof coupled to a radiologic (e.g., $I^{125}$) or other imaging molecules (e.g., dyes, pigments or fluorescent molecules such as luciferase, fluoroscein or commercially available fluorescent molecules from quantum.com). The antibodies may be coupled to the radiologic or imaging molecule by methods known in the art.

Examples of therapeutic moieties include, but are not limited to, ricin, radioisotopes, clotting agents, thrombolytic factors, chemotherapeutic and radiosensitizing agents, anti-angiogenesis agents, anti-motility agents, and immunomodulatory agents. Examples of a detection moiety include, but are not limited to, radioisotopes, dyes, pigments, or fluorescent molecules such as luciferase, fluoroscein or commercially available fluorescent molecules from quantum-corn. The polypeptide may be coupled to the radiologic or imaging molecule by methods known in the art and used to target delivery of the therapeutic or detection moiety to the liver.

Design of Methods of Treatment

The diagnostic and prognostic methods as described herein, as well as methods that predict or identify survival rates, such as for example, five and ten year survival rates, can be used to design appropriate therapeutic intervention. For example, for an individual with an early stage of a condition, methods for detecting the presence of elevated cumulative levels of any one or more of a polypeptide of SEQ ID NOs 14-23, or polynucleotides encoding such polypeptides (SEQ ID NOs 1-13), can help a physician determine if frequent diagnostic assessment is necessary or if therapeutic intervention is necessary. A physician will be able to determine appropriate therapeutic intervention based on the methods disclosed herein and conventional methods known in the art.

In some examples, the method comprises administering to a subject in need of such treatment a targeting domain linked to a therapeutic agent in an amount effective to treat the condition, or an effective amount of a composition that inhibits the condition (e.g., collection of phage or phage expression products identified by the method herein; a targeting domain linked to a therapeutic agent and/or an antibody directed against a polypeptide comprising a targeting domain).

In other examples, provided herein are kits and compositions comprising one or more polynucleotide (e.g., one or more of SEQ ID NOs 1-13, or polynucleotides that, due to the degeneracy of the genetic code, encode the same or substantially the same amino acid sequence as that encoded by one of the specified polynucleotides) or reagents specific thereto, such as antibodies, specific for couple moieties described herein.

In addition, the present invention provides kits comprising primers specific for polynucleotides encoding any one or more of developing microvasculature homing polypeptide(s), such as CVE homing polypeptides (e.g., any one of the polypeptides encoded by any of SEQ ID NOs 1-13). Such kits comprise primers specific for such polynucleotides, and, optionally, primers for control polynucleotides and instructions for use.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

The following examples illustrate embodiments of the invention, but should not be viewed as limiting the scope of the invention.

Novel strategy for unbiased identification of high affinity molecules homing to endothelial cells lining the vasa vasorum.

Example 1

Generation of cDNA Phage Libraries

A phage library carrying large fragments of expressed proteins from the bone marrow (BM) was generated (see FIG. 1). As a source of BM expressed genes, the particulate fractions (>50 micron particles filtered out) that are discarded after human bone marrow harvests were used. This particulate fraction cannot be transfused to patients receiving BM transplant due to the large particle size, but, contains bone marrow matrix-bound cells (stem and progenitor cells not released into the circulation), precursor cells and differentiated cells. Cells were derived from different donors and stimulated by attachment and with growth factors. cDNA libraries of human bone marrow cells were constructed as follows: Human bone marrow cells were harvested from healthy donors and filtered through a 200 µm filter. Mononuclear cells were isolated by gradient centrifugation (Ficoll-Paque PLUS, GE). Mononuclear cells were grown in DMEM cell culture medium containing 50 ug/ml SCF, 10 ng/ml GM-CSF and 10 ng/ml IL-3 and the non-attached cells were harvested after 3 weeks in order to select for hemapoetic precursor cells. Mononuclear cells were cultivated in MesenCult (Stemcell Technologies Inc) for 2 weeks and the resulting attached mesenchymal precursor cells were isolated. Mononuclear cells were isolated from mononuclear cells by utilizing a negative selection system (Stemcell Technologies Inc). Monocytes were isolated by utilizing a negative selection system (Stemcell Technologies Inc.) from mononuclear cells, which were previously harvested by gradient centrifugation. From each cell type cDNA was generated by reverse transcribing mRNA using random primers and oligo-dT oligonucleotide. From the RNA of the four collected pools of bone marrow derived cells (mononuclear cells, hematopoetic precursor cells, mesenchymal precursor cells and monocytes) cDNA was generated by reverse transcribing using random primers and oligo-dT oligonucleotides. Following second strand synthesis, gel filtration was performed to size fractionate the cDNA, which resulted in exclusion of all products less than 200 base pairs in size. Subsequently, the cDNA was EcoR1/HindIII double digested and directionally cloned into a multiple cloning site within the capsid encoding gene 10B of bacteriophage T7 using the OrientExpress Cloning System (Novagen, Darmstadt, Germany). The quality of the resulting inserts was verified gel electrophoresis. The insert sizes of cDNA in the phage display library ranged between 100 to 2,000 with the majority between 300 and 900 nucleotides, which results in the display of a majority of 100 to 300 amino acids of protein fragments to be expressed on the phage surface.

The resulting phage libraries were estimated to comprise between 1 and $4 \times 10^6$ clonal species. Amplification of phage libraries was carried out by inoculation of BLT5615 E. coli (Novagen) stocks. Following E. coli lysis, phage was isolated by collection of the media supernatant; titering of the phage stock was performed using a serial dilution plating assay. For phage in vivo selection assays all phage libraries were pooled.

Bacteriophage (or "phage"), are viruses that infect bacteria. After binding to the bacterial cell surface, they inject their DNA into the host, capture the bacterial biosynthetic machinery, and then proliferate, resulting in millions of virus copies. The success of the phage fishing strategy derives from the ability to genetically alter the phage to: 1) express molecules of interest; 2) use in one experiment millions of phage with millions of different peptides to be examined for targeting capacity; and 3) expand individual phage so that millions of the particular phage of interest are easily available for further study.

The specific strategy developed is based on the capacity to genetically alter millions of bacteriophage so that each phage expresses a single relatively large peptide. This is achieved by inserting a random library of millions of cDNAs into the genome of bacteriophage that have been specially designed so that each phage displays on its surface one copy of a single fusion protein of 100 to 1,000 amino acids. In an experiment to determine which peptides bind to endothelium within the target tissue ("fishing" for the phage), millions of genetically altered phage are injected into an animal. Those that specifically bind to the tissue are isolated and expanded by infecting susceptible bacteria and harvesting the expanded phage particles. In aggregate, therefore, millions of different peptides can be examined as potential targeting molecules.

Thus, the phage fishing technique, through the binding of phage-expressed ligands to tissue-specific endothelial receptors, allows identification of tissue-specific ligands that are, in effect, functioning as molecules that home to the target tissue.

Example 2

Homing to Collateral in Ischemic Vessels

Figure 2:
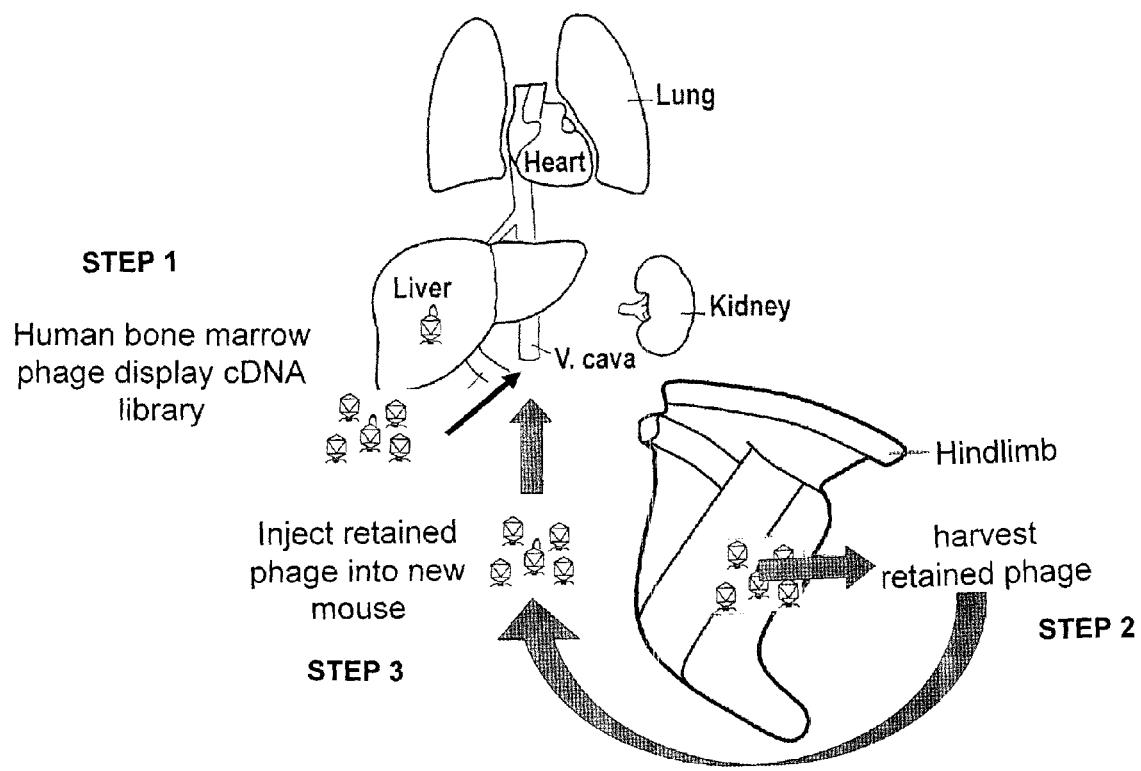
FIG. 2 depicts a schematic describing the general concept of the selection of phage homing to collaterals in the ischemic hindlimb collateral model. Step 1: A human bone marrow phage display cDNA library, as described in FIG. 1, is injected into the vena cava inferior. From there the phage through the right ventricle of the heart, the lungs, the left ventricle and then travel to the femoral artery and the collaterals. The animal was flushed with saline to remove all residual blood and trapped phage particles that did not bind specifically. Step 2: Phage particles retained by collaterals after the flushing of the animal were then rescued by dissecting out the collateral, homogenization and addition of the host bacteria. Step 3: Phage particles rescued were expanded and after growing up a high enough concentration injected again into a new series of animals for a further round of selection from the collateral in the hind limb.

Collateral development (collaterogenesis) is an important compensatory response to obstructive arterial disease. For the selection of particles binding to receptors on endothelia in collateral vessels, the ischemic hindlimb model was used (see FIG. 2): Step 1: The human bone marrow phage display cDNA library described above was injected into the vena cava inferior. From there the phage pass through the right ventricle of the heart, the lungs, the left ventricle and then travel to the femoral artery and the collaterals. The animal was flushed with saline to remove all residual blood and trapped phage particles that did not bind specifically. Step 2: Phage particles retained by collaterals after the flushing of the animal were then rescued by dissecting out the collateral, homogenization and addition of the host bacteria. Step 3: Phage particles rescued were expanded and after growing up a high enough concentration injected again into a new series of animals for a further round of selection from the collateral in the hind limb.

Phage were selected 1 day and 4 days after ischemia, since different surface molecules were expressed under those conditions.

Six to eight weeks old C57 ApoE$^{-/-}$ mice underwent ischemic hindlimb surgery (Couffinhal, T. et al. Mouse Model of Angiogenesis. American Journal of Pathology 152: 1667-1679. 1998; Stabile, E. et al. Circulation, Impaired Arteriogenic Response to Acute Hindlimb Ischemia in CD-4 Knockout Mice, 2003).

Collaterals were targeted with phage either 24 h or 4 day post surgery. For selection of phage homing to the ischemic hind limb of a ApoE−/− mouse, $10^9$ pfu phage were injected into the vena cava in the opened abdominal space. Unbound phage was washed out with the blood by injecting 10 ml saline directly through the heart. Selected phage retained in the hindlimb collateral circumventing the ligated artery was harvested, amplified and reinjected repeatedly into the next mouse. In order to harvest the bound phage, the collateral vessel and control organs were removed from the mouse and homogenized. The bound phage in the supernatant was amplified in E. coli.

Titering of the selective phage after each round was performed using a serial dilution assay. Phage homing to collaterals 24 h post surgery were selected in three rounds—each round with two to three mice. Whereas phage homing to collaterals 4 days post surgery were selected in two rounds—each round with two to three mice. In parallel with animals with ischemic hindlimbs (1 day or 4 days post surgery, respectively), control animals were also assessed for phage homing by a parallel injection and harvesting of phage from the same organs.

From each last round, single phage were isolated, amplified and the cDNA-insert was sequenced using the T7-UP primer (Novagen, Darmstadt, Germany).

Figure 3:
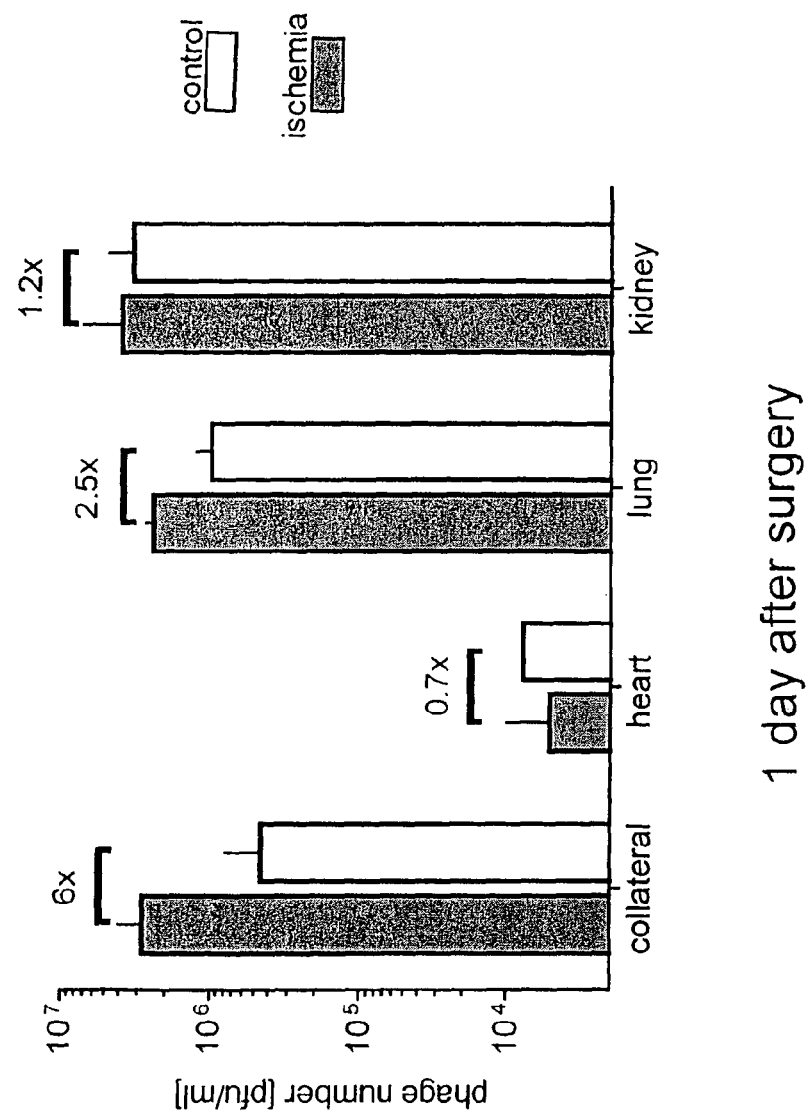
FIG. 3 depicts a bar graph showing the organ homing of phage selected from collaterals in ischemic hindlimbs at 1 day after surgery. Titers of phage (phage number [pfu/ml, plaque-forming units per milliliter) homed into the collaterals, hearts, lungs, kidneys of the same animals were obtained after the third round of selection. Typically data from 2 to 3 animals are represented (mean+/−SE). In parallel with animals with ischemic hind limbs (1 days post surgery), control animals were also assessed for phage homing by a parallel injection and harvesting of phage from the same organs. A 6-fold higher titer in ischemic collaterals versus control was found. In addition, in another vascular bed of muscular tissue, the hearts from the animals with ischemic hind limbs retained 0.7-fold phage than control animals. This means that between two vascular beds in muscular tissues, the phage particle inserts selects approximately 10-fold in favor of the ischemic vascular bed. A further comparison is with the lung vascular bed, where the selection is somewhat in favor of the animals with ischemic hind limbs (2.5-fold) which means that the relative selectivity towards the collaterals in the hindlimb is only 2.4-fold (6/2.5). For the kidney vascular bed the selectivity is 5-fold (6/1.2).

FIG. 3 shows the results obtained for phage homing to collaterals 24 h post surgery. A 6-fold higher titer in ischemic collaterals versus control was found. In addition, in another vascular bed of muscular tissue, the hearts from the animals with ischemic hind limbs retained 0.7-fold phage than control animals. This means that between two vascular beds in muscular tissues, the phage particle inserts selects approximately 10-fold in favor of the ischemic vascular bed. A further comparison is with the lung vascular bed, where the selection is somewhat in favor of the animals with ischemic hindlimbs (2.5-fold) which means that the relative selectivity towards the collaterals in the hindlimb is only 2.4-fold (6/2.5). For the kidney vascular bed the selectivity is 5-fold (6/1.2).

Figure 4:
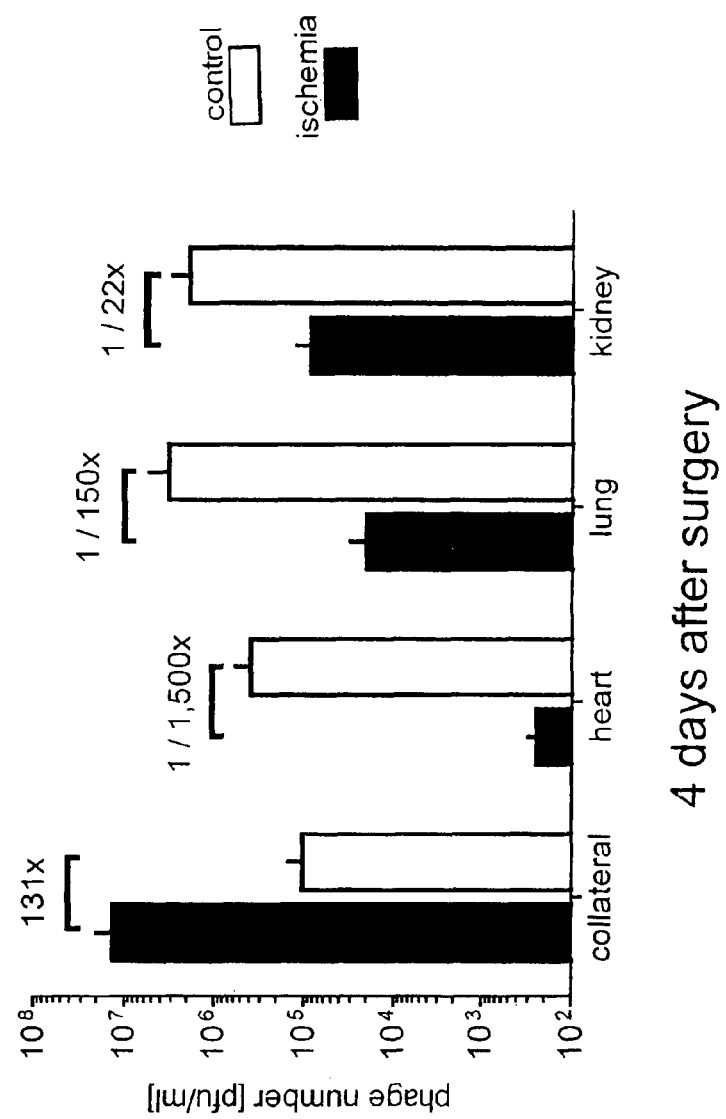
FIG. 4 depicts a bar graph showing the organ homing of phage selected from collaterals in ischemic hindlimbs at 4 day after surgery. Titers of phage (phage number [pfu/ml, plaque-forming units per milliliter) homed into the collaterals, hearts, lungs, kidneys of the same animals were obtained after the third round of selection. Typically data from 2 to 3 animals are represented (mean+/−SE). In parallel with animals with ischemic hind limbs (4 days post surgery), control animals were also assessed for phage homing by a parallel injection and harvesting of phage from the same organs. A 131-fold higher titer in ischemic collaterals versus control was found. In addition, in another vascular bed of muscular tissue, the hearts from the control animals retained 1,500-fold more phage than those from the animals with ischemic hind limbs. This means that between two vascular beds in muscular tissues, the phage particle inserts select 200,000-fold in favor of the ischemic vascular bed. A further comparison is with the lung vascular bed, where the selection in favor of the ischemic hind limb is 20,000-fold (131×150) and the kidney vascular bed where the selection is 2,900-fold. Applicants conclude that the phage selection worked highly effectively. Applicants further conclude that the phage selection in the collateral in the ischemic hind limb after the one day ischemia is by far not as effective and selective as that seen after 4 days (see FIG. 3 versus FIG. 4). Applicants interpret this to mean that possibly the remodeling within one day and significant surface changes or expression of differential surface molecules in the ischemia-induced collaterals has only started at day 1 and is more advance at day 4.

FIG. 4 shows the results obtained for phage homing to collaterals 4 days post surgery. A 131-fold higher titer in ischemic collaterals versus control was found. In addition, in another vascular bed of muscular tissue, the hearts from the control animals retained 1,500-fold more phage than those from the animals with ischemic hindlimbs. This means that between two vascular beds in muscular tissues, the phage particle inserts select 200,000-fold in favor of the ischemic vascular bed. A further comparison is with the lung vascular bed, where the selection in favor of the ischemic hindlimb is 20,000-fold (131×150) and the kidney vascular bed where the selection is 2,900-fold. Applicants conclude that the phage selection worked highly effectively. Applicants further conclude that the phage selection in the collateral in the ischemic hindlimb after the one day ischemia is by far not as effective and selective as that seen after 4 days (see FIG. 3 versus FIG. 4). Applicants interpret this to mean that possibly the remodeling within one day and significant surface changes or expression of differential surface molecules in the ischemia-induced collaterals has only started at day 1 and is more advanced at day 4.

Example 3

Homing Gene Expression

Figure 8:
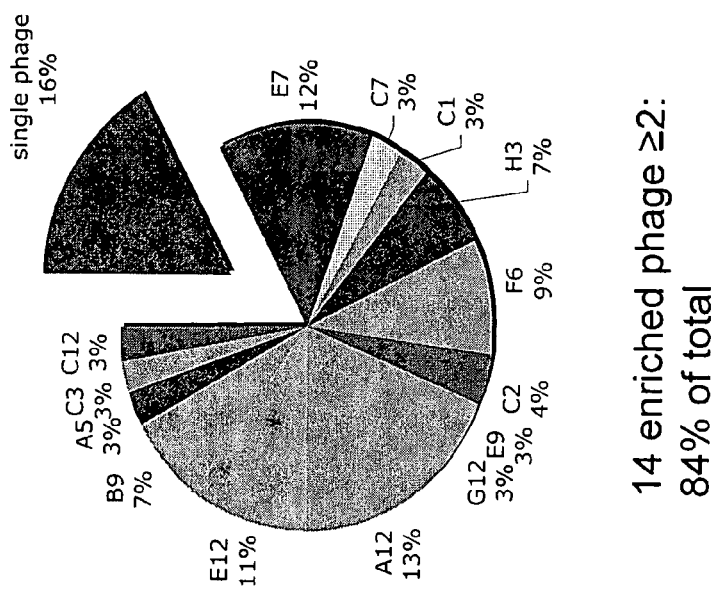
FIG. 8: A total of 14 distinct phage were obtained from sequencing of approximately 100 inserts from randomly selected phage. Out of these, 4 were only found in the day 4 ischemia selection, 5 were unique for the day 1 ischemia and 5 were found in both preparations. Different and overlapping molecules may serve to recognize the altered surface in the endothelia of collaterals after 1 and 4 days of ischemia.

A subgroup of phage that binds to vascular beds was selected after injection into vessels and circulation in the blood stream for short times. Selected phage that bind with high affinity in vivo to targeted vessel beds (diseased or healthy) were harvested and the inserts that drive this homing were identified by DNA sequencing. A total of 14 distinct phage were obtained from sequencing of approximately 100 inserts from randomly selected phage. Out of these, 4 were only found in the day 4 ischemia selection, 5 were unique for the day 1 ischemia and 5 were found in both preparations (see FIG. 8). Different and overlapping molecules may serve to recognize the altered surface in the endothelia of collaterals after 1 and 4 days of ischemia. The sequences of phage inserts A5, A12, B9, C1, C2, C7, E7, E9, E12-1, E12-2, F6, G12 and H3 (SEQ ID NOs: 1-13, respectively) are shown in FIGS. 6A, B, C. See also the Table, which presents a summary of the sequences identified.

Figure 5:
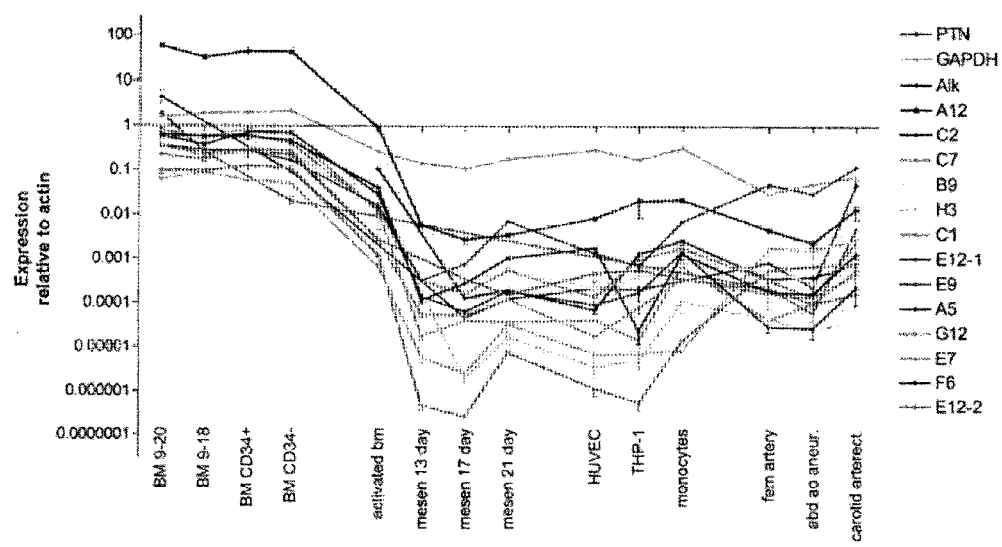
FIG. 5 depicts a graph showing the mRNA expression levels, as fold-expression relative to actin, of the collateral homing gene fragments in different human tissues and cell lines by real-time PCR. For these measurements, RNA was extracted from freshly harvested human bone marrow (BM), BM cultivated short-term with activating growth factors, monocytes isolated from BM, BM cultivated for 13 and for 17 days, the human monocytic cell line THP-1 and primary human umbilical vein endothelial cells (HUVEC). Extracted RNA was then reverse transcribed and the levels of expression detected real-time PCR with specific primer pairs. Actin mRNA levels were used as an internal standard for each sample set and results for each of the selected gene fragments are given relative to actin. GAPDH is another loading and quality control used. The expression levels are presented on a logarithmic scale since they cover a wide range of one million-fold when comparing the highest and lowest levels observed. The results show that most of the selected homing genes are down-regulated during differentiation of human bone marrow to more mature cells. We conclude that the homing gene expression is the highest in haematopoietic precursor cells and reduced or lost during differentiation.

For cell expression studies RNA was isolated from cells, reverse transcribed and the resulting cDNA was analyzed by real-time PCR with primer pairs specific for each phage insert (see FIG. 5). For these measurements, RNA was extracted from freshly harvested human bone marrow (BM), BM cultivated short-term with activating growth factors, monocytes isolated from BM, BM cultivated for 13 and for 17 days, the human monocytic cell line THP-1 and primary human umbilical vein endothelial cells (HUVEC). Extracted RNA was then reverse transcribed and the levels of expression detected real-time PCR with specific primer pairs. Actin mRNA levels were used as an internal standard for each sample set and results for each of the selected gene fragments are given relative to actin. GAPDH is another loading and quality control used. The expression levels are presented on a logarithmic scale since they cover a wide range of one million-fold when comparing the highest and lowest levels observed. The results show that most of the selected homing genes are down-regulated during differentiation of human bone marrow to more mature cells. We conclude that the homing gene expression is the highest in hematopoietic precursor cells and reduced or lost during differentiation.

Example 4

Identification of the Peptide Sequence of Expressed Homing Genes

FIG. 7 lists the sequences of fusion proteins with gene 10 identified by mass spectrometry of T7 phage expressing the different collateral homing sequences A5, B9, C2, C7, E7, E9, E12, F6, G12 and H3 (SEQ ID NOs: 14-23, respectively) produced in E. Coli. Without frame shift, only very short peptides (<6 amino acids) were typically produced.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

TABLE summary of found sequences

| Gene locus (Blastn result) | phage | insert length blast homology | intron of known gene | NCBI reference | remarks | targeted collateral | Enrichment | Total | |
|---|---|---|---|---|---|---|---|---|---|
| chrom 21q | C7 | 488 | no | | | 4 day co | 1 | 2 | |
| | | | | | | 24 hrs isch. | 1 | | |
| CTD-2005A22 | C1 | 375 | RXFP1 relaxin/ insulin-like family peptide receptor 1 between exon 11 and exon 12 | GeneID: 59350 | previously: Leucine rich repeat containing G protein coupled receptor 7 | 4 day co. | 1 | 2 | only 4 day |
| | | | | | | 4 day isch. | 1 | | |
| RP11-332M12 | H3 | 607 | no | | | 24 hrs isch. | 5 | 2 | only 24 hr |
| RP11-354H21 | E7 | 600 | no | | | 4 day isch. | 7 | 10 | |
| | | | | | | 24 hrs isch. | 2 | | |
| | | | | | | 24 hrs control | 1 | | |
| RP11-338L20 | F6 | 433 | no | | | 4 day isch. | 7 | 7 | only 4 day |
| RP11-442E11 | C2 | 476 | no | | | 4 day co. | 1 | 3 | |
| | | | | | | 24 hrs isch. | 2 | | |
| RP11-73O12 | E9 | 345 | ALCAM between first and second exon | GeneID: 214 | CD166 | 24 hrs isch. | 2 | 2 | only 24 hr |
| RP11-809C23 | G12 | 359 | no | | | 4 day isch. | 1 | 2 | |
| | | | | | | 24 hrs isch. | 1 | | |
| RP11-82P9 | A12 | 393 | no | | | 24 hrs isch. | 7 | 10 | only 24 hr |
| | | | | | | 24 hrs control | 3 | | |
| RP1-47M23 | E12-1 | 567 | no | | Phage E12 contains E12-1 and | | | | |
| RP11-85C4 | E12-2 | 175 | NRXN1 Neurexin 1 between exon 5 and exon 6 | GenID: 9378 | E12-2 sequences | 4 day isch. | 8 | 8 | only 4 day |
| RP4-676L2 | B9 | 925 | no | | | 4 day co | 2 | 5 | |
| | | | | | | 24 hrs isch. | 3 | | |
| | A5 | 380 | DMD dystrophin between first and second exon | GeneID: 1756 | | 24 hrs isch. | 2 | 2 | only 24 hr |

| only 4 day phage enrichment | only 24 hr phage enrichment | enrichment in both time points |
|---|---|---|
| C1 | H3 | C7 |
| F6 | E9 | E7 |
| E12 | A12 | C2 |
| | A5 | G12 |
| | | B9 |

What is claimed is:

1. A developing vessel homing polypeptide comprising the amino acid sequence PTLAVYSPHRLVMFIFIMIRKKHH-FLLWLYAYFM (amino acid residues 14-47 of SEQ ID NO: 18).

2. The homing polypeptide of claim 1 coupled to a therapeutic moiety.

3. The homing polypeptide of claim 2, wherein the therapeutic moiety is ricin, a radioisotope, a clotting agent, a thrombolytic factor, a chemotherapeutic agent, a radiosensitizing agent, an anti-angiogenesis agent, an anti-motility agent or an immunomodulatory agent.

4. A pharmaceutical composition comprising (a) the homing polypeptide of claim 1, (b) a therapeutic agent and (c) a pharmaceutically acceptable carrier.

5. The pharmaceutical composition of claim 4, wherein the therapeutic agent enhances collateral development or decreases microvasculature development.

6. A pharmaceutical composition comprising (a) the homing polypeptide of claim 1 coupled to a therapeutic moiety and (b) a pharmaceutically acceptable carrier.

7. A kit comprising the homing polypeptide of claim 1.

8. The homing polypeptide of claim 1 encoded by SEQ ID NO:7.

* * * * *

SEQUENCE LISTING

<160> NUMBER OF SEQ ID NOS: 23

<210> SEQ ID NO 1
<211> LENGTH: 445
<212> TYPE: DNA
<213> ORGANISM: Artificial Sequence
<220> FEATURE:
<223> OTHER INFORMATION: Synthetic Oligonucleotide

<400> SEQUENCE: 1

```
ggggattcag gggcagttta taattcagtc acatgttaaa gaacaaaaag gacgaaagaa      60
gaataaagca gatagaatcg tgaaatgggt tacattattt gcaccataaa gtttaagtaa     120
atcaaattat tgggaatatt ctgagataga gctaaagtct ttctcaagag tcatggttga     180
aaccacatgt tgtggaggaa ctgatggtga ttgttgcccc attgtgggat tcctccctat     240
ggtaatgaca tcaaaatgaa aaaaaaaaaa cacacacaca caaaaaaatg acgcaaattg     300
taattaaagg tggagctgtt tatgatctgg ttatctccac attgttctgg gaaaaaattg     360
aaacattact gggtcaaatc atgtctgtga aacaaaatga aggtaaaaa tagtgaataa      420
aaaaaaaaaa attaaaaaca agctt                                           445
```

<210> SEQ ID NO 2
<211> LENGTH: 431
<212> TYPE: DNA
<213> ORGANISM: Artificial Sequence
<220> FEATURE:
<223> OTHER INFORMATION: Synthetic Oligonucleotide

<400> SEQUENCE: 2

```
gcgattcaac actctataag aaaaaatata ataatttgat ttaaaaactg gcaaaatatc      60
tgaatagata tttctcaaaa gaagacatac gaatggcaaa caagcataca aaaaggtgtt     120
caacatcatt gatcatcaga gaaatgcaaa tcaaaactac aaggaaaata tcatctcact     180
cctgttaaaa tggcttttat gcaaaagtca gacaataaca aatgctgaaa aggatgtgga     240
aaaaaggaaa ccctcatgca ctattggtgg aatgtaaatt aatacagcca ctacggagaa     300
cagtttgcag gttcctcaac aacaacaaca aaaaactaaa aacagagcta tcttacaatc     360
caacaattcc actcccagat atatatcaga agtaaggaaa tgacactaag ttttgaaaa      420
atgaaaagct t                                                          431
```

<210> SEQ ID NO 3
<211> LENGTH: 1040
<212> TYPE: DNA
<213> ORGANISM: Artificial Sequence
<220> FEATURE:
<223> OTHER INFORMATION: Synthetic Oligonucleotide

<400> SEQUENCE: 3

```
gcgattctgg gactgtggat atagcttgcc acagtatctt atcagttaat tgcattcttg      60
aatgtgctgg gagtcagctt gcacaaggta agtccttgag gaaggggctg ccagtgtaag     120
agccaagatg gagtctgtct ggctctctta gctaagggag agtcaattca ggtggaaaca     180
aggctaggtg attaaaggaa agggagagtc taaaaacagg gttagtaaaa accaggttgg     240
gcattacagt atcacccaga caaccaagtg ttcatgttta accacaaagc cctcttgtaa     300
ttgctgaagg gtatttgctt gtaattgctg cgaccattct tcaagttgtt tctttaactc     360
acattcaaga gtagaaattt gagaagaaat acggttgtga taagccccct gcaggtgtgc     420
```

```
tttcactctc tcccaagcat attgggagct attatatggc agaggtgtga cacagatagg    480
attatattgc caatcacaat gtaaattttg atgggtaatg aatgcctgct gctgaccccc    540
cagccattca actgcggctt caagagcctc caggtgagac agaatagttt tatcaatatt    600
tacctgttcc tgaaattcat gggttacatt atataccatg tggttcacca ctgaggctat    660
gtgaatagat cctgttagag agacagctgc agtagcagca gttgctagta tgataatagc    720
tgagactaaa aagtcaatta aagtggccag aaatcttttt ttctgagcat gagacagtgc    780
ttttctaaat agctgctggg tggaatttcc ttcccagctc caggttaaat ttacaggcag    840
ccacatttct gcatgccgtt ttaatcatga cgttatactt aactgtgtaa cgttttgata    900
acagcatgta gcataccagt actggaagac tttatactat actgattctg ttttttgtaac   960 ctcgccaaag tatatgggtg catagtaaca ctgtcagtat atgcaaagtg ctgccttata   1020
ctccctaaaa caatcagaaa                                                1040

<210> SEQ ID NO 4
<211> LENGTH: 275
<212> TYPE: DNA
<213> ORGANISM: Artificial Sequence
<220> FEATURE:
<223> OTHER INFORMATION: Synthetic Oligonucleotide

<400> SEQUENCE: 4
acattctgtg ggatgatggt gatggtagca tagcatatga atgtgcttaa tgcctctgaa     60
ggtagactta aaaatggtta agatgccaca ttttatgtta tgtgtatttg atgacgatta    120 aacatttta aaaattgaaaa aggtaaacat tacaaaataa tttagtgaag ccagatatca    180
tgtcacttca tgtttctgtt aaatttatgt acaattaggc tggtttgtat ttagaaattc    240
tagttataaa gatgaatgaa taacagccaa agctt                                275

<210> SEQ ID NO 5
<211> LENGTH: 370
<212> TYPE: DNA
<213> ORGANISM: Artificial Sequence
<220> FEATURE:
<223> OTHER INFORMATION: Synthetic Oligonucleotide

<400> SEQUENCE: 5
gcattcagac cagcttggtc acagagagag agtccatctc tataaaaaaa tgtttaaaaa     60
ttagacgggc atgatggtgc ttggtgcttg cctgtagtcc cagctacttg ggaggctgag    120
gtgggaggac tgcctgagcc caggaactgg agattgcagg aagctatgat cacatcactg    180
cactccagcc tgggtgacag agcgagactc cgtctcaaaa aaaagtcttt tgttttcagt    240
catggtggta tacgcctcta gtctcagcta cttgggagac tgaggcagga gggtcacttg    300
aacccaggag ttcgagttca gtctggacaa aatagcaaga ccccatctct aaatcaagca    360
aacaaagctt                                                            370

<210> SEQ ID NO 6
<211> LENGTH: 503
<212> TYPE: DNA
<213> ORGANISM: Artificial Sequence
<220> FEATURE:
<223> OTHER INFORMATION: Synthetic Oligonucleotide

<400> SEQUENCE: 6
cgattcagcg cttgattcca ttactgggta tatacccaaa ataatataaa ttgttggact     60
ataattatac atgcatgtgt gtgttcataa cagcactatt cataacagca aagacatgaa    120
```

| | |
|---|---|
| atcaacctaa atgcccatca aaggcagatt gagcaaagca aatatggtag atacacacca | 180 |
| tggatgctat gcagccataa aaatgaaaaa gatcatgtcc tttccagaaa catggatgaa | 240 |
| gttggaggcc attatcctta gcaaactaat gcaggaacaa aaaccaaat gctgcgtgtt | 300 |
| ctcactgata agtgggagct aaatgatgag aacagcagac acatagaggg gacaacagac | 360 |
| actggggtct actggaaggt ggagggtgag aggagggaga ggatcaggaa aaataactaa | 420 |
| caggcactag gcttaatact tgggtgacga ataatctgt acgacaaacc cctatgacaa | 480 |
| gggtttactt atataataag ctt | 503 |

<210> SEQ ID NO 7
<211> LENGTH: 352
<212> TYPE: DNA
<213> ORGANISM: Artificial Sequence
<220> FEATURE:
<223> OTHER INFORMATION: Synthetic Oligonucleotide

<400> SEQUENCE: 7

| | |
|---|---|
| cgattgcaga agcgtcaggt tttgtaacct acgcttgcag tttactctcc ccatagactt | 60 |
| gtaatgttta tctttataat gataaggaaa aacatcact ttctgttatg gcttatgcc | 120 |
| tattttatgt agtacagaat aaacctaata aaatgatgtt gggattgttc cataaggcat | 180 |
| tctaaaactt cttcttccta gtagttgaat tagagttttt agtcattaat aagacacatg | 240 |
| gcatcataaa aacacaaaat ctgaaataaa aagaaagatg ttttgtccag gattcagaaa | 300 |
| aatatttgt ctccattttg ccatatgctt catgagatct tgtactaagc tt | 352 |

<210> SEQ ID NO 8
<211> LENGTH: 351
<212> TYPE: DNA
<213> ORGANISM: Artificial Sequence
<220> FEATURE:
<223> OTHER INFORMATION: Synthetic Oligonucleotide

<400> SEQUENCE: 8

| | |
|---|---|
| ggggaataat tttgttatgg gctagtgaaa agtatttgct ttcctaaggt atgagcatgt | 60 |
| actggttcac taacttccca gttgttttc tggctgagaa gagcttttct tctggtggca | 120 |
| catgtccatg acagctgttt attccacatg tttccattga agcatatta acctgagcaa | 180 |
| atggggataa ttatcacagt gtaaaaatgc ctttggatgt taatgattcc tcttctgtcg | 240 |
| tctcctttga ttggcctgac cctcgtatta ctatgtatta atatccttag atcttcatgg | 300 |
| taccaaggac attccaaaag tcatccacat tgactttggc tcagaaagct t | 351 |

<210> SEQ ID NO 9
<211> LENGTH: 566
<212> TYPE: DNA
<213> ORGANISM: Artificial Sequence
<220> FEATURE:
<223> OTHER INFORMATION: Synthetic Oligonucleotide

<400> SEQUENCE: 9

| | |
|---|---|
| ggatacttgc tagtaggcta ctgcattcat ttgggctcca ccctttaaga ggggcattaa | 60 |
| caaggtgaag tgtattcctg ggtcagtggc agctggtctc actagcatgt ccctaggagg | 120 |
| acagacagca tagaagggcc ctgggaactt gtgccctggg aactgggtgc cagaactggg | 180 |
| gacgtttaaa aataacaatc tggagcaaat atgatgactc ttttaattt tttcaaagac | 240 |
| tgagatttgg aagaggagtt gatctgtgct gggagaccct ggcaacagt aggtagaagt | 300 |
| gacagggagg tggagtggtt aaactttcta ataatcaatg ctggttgaca acaaaataga | 360 |

```
ctgcctcaat tatattgcat agagacctgc agttgtatta caaccctctt tagcaagcca    420
ccaggaaaat tggtgcaaag gagaaagatt gctatggtat gaatcactct tttggctgtg    480
tagatgggta tgaatgtttg tctctgtcac aggaagtatg gatgccacct ggaagatgac    540
ctatgtgtag aaggaaaccc aagctt                                         566
```

<210> SEQ ID NO 10
<211> LENGTH: 169
<212> TYPE: DNA
<213> ORGANISM: Artificial Sequence
<220> FEATURE:
<223> OTHER INFORMATION: Synthetic Oligonucleotide

<400> SEQUENCE: 10

```
gcaaggtata atacagttac gcataatatg agattagcgg acttgcacga tttaaggttt     60
tgttttaatt ttaatcaccc agagagctgc cagttgttct gatgcctctt tggttaagtg    120
aagctgaaaa aagggtataa ctcaactgtc acatgaatta cggaagctt                169
```

<210> SEQ ID NO 11
<211> LENGTH: 483
<212> TYPE: DNA
<213> ORGANISM: Artificial Sequence
<220> FEATURE:
<223> OTHER INFORMATION: Synthetic Oligonucleotide

<400> SEQUENCE: 11

```
gaattggggc atataatgaa acaatggtc gggaaatgga agagatatat taaccgaatg     60
ggtctggaaa taaataagt aaagaacaac tttattccct gctctttgtg gcttgtgcaa    120
cctcatgaga caaatggatg caccaggaat ccagctgtaa tatacaactg tcagagaaac    180
acttttaagc aaagtacaat gtcctgtgag agtcacgtaa tgattaattt tgatttgatt    240
aacatttttg cttaataaat ttgttatagt aaataaacta atttgtttag aaaacagcac    300
cagtccttgt tcaacacatt tcataaagaa gttcatccat ggtttcaata tgcacccttg    360
attattctat ggagagttaa ataataattt tataactttg gagatattaa aggggggtt    420 atatatctct tcattcagtc tcctatatat tcagacagaa aaactgagga caaaataaag    480
ctt                                                                 483
```

<210> SEQ ID NO 12
<211> LENGTH: 392
<212> TYPE: DNA
<213> ORGANISM: Artificial Sequence
<220> FEATURE:
<223> OTHER INFORMATION: Synthetic Oligonucleotide

<400> SEQUENCE: 12

```
ataaaaggaa gcagctttaa gggaagcaac ttcaattgag tgcattgagg gcaaaacagc     60
caaagggtga tcctgaatta gtttatatga cgtaaaatgc aaaacagtaa agcctgttat    120
ctaaaggaaa agataaaagg caaaggcaga gtcaaagata gcagatttca gcagtcatag    180
atttctctct ctggaaagca cagctgtttt ttgtatctgc caacctaatg gaactcctca    240
aatgactttt gttgaaagcc cacaggtcct ggcagggcat acaagaactt gagaacacat    300
ggattctttc tttcaggacc ttacatttta aaaaggattc accatgagaa ctcaatggaa    360
aactgatctg gtgaagggggg aaagacaagc tt                                 392
```

<210> SEQ ID NO 13
<211> LENGTH: 639
<212> TYPE: DNA

<213> ORGANISM: Artificial Sequence
<220> FEATURE:
<223> OTHER INFORMATION: Synthetic Oligonucleotide

<400> SEQUENCE: 13

```
caaacacagg gtgattaagt tactctctag aagaacaaat accataggag cccagactgg    60
ctttagtgat gatataagta aagaaaagca catttcaaaa agcaaagaaa tgacagtgct   120
aatttacttg cccaaatgtt actgagagaa ctgtcacttg aatgtctctc agaaatcata   180
aggtggtgaa tgacactctt tgtcatcagt atatccatag acaatgatt gttctgaagc    240
aaaatcttga atttcttact ctcttaacag gcggacctca ggaaataatg aatcttgata   300
aaagcatgta atttcacact attttaaatt gaggttctat gtcatttac tgtgatatat    360
ttcctgttgc tcctttaaaa tgagtattta cattaaaatt atttcactta aatgaataaa   420
acattaacaa caataatgca gcatgcacat ttaaatggag gatcgacatg attagaagtg   480
catctcaaag gatttccctt tgttttctga ttgttgcccc ctctgataga tgattcatta   540
atttcttgtc acttggagta aataggtggt tagaaaggtc tagtataaat aaaaatattt   600
ttctactttg ttttcatttt tcaaaattct aacaagctt                          639
```

<210> SEQ ID NO 14
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 14

```
Phe Lys Gly Gln Phe Ile Ile Gln Ser His Val Lys Glu Gln Lys Gly
 1               5                  10                  15
Arg Lys Lys Asn Lys Ala Asp Arg Ile Val Lys Trp Val Thr Leu Phe
            20                  25                  30
Ala Pro
```

<210> SEQ ID NO 15
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 15

```
Glu Phe Leu Gly Thr Val Asp Ile Ala Cys His Ser Ile Leu Ser Val
 1               5                  10                  15
Asn Cys Ile Leu Glu Cys Ala Gly Ser Gln Leu Ala Gln Gly Lys Ser
            20                  25                  30
Leu Arg Gly Leu Pro Val
        35
```

<210> SEQ ID NO 16
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 16

```
Phe Lys Thr Ser Leu Val Asn Arg Glu Arg Val His Leu Tyr Lys Lys
 1               5                  10                  15
Met Phe Lys Asn
            20
```

```
<210> SEQ ID NO 17
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 17

Phe His Tyr Trp Val Tyr Thr Gln Asn Asn Ile Asn Cys Trp Thr Ile
1               5                   10                  15

Ile Ile His Ala Cys Val Cys Ser
            20

<210> SEQ ID NO 18
<211> LENGTH: 47
<212> TYPE: PRT
<213> ORGANISM: Artificial Sequence
<220> FEATURE:
<223> OTHER INFORMATION: Synthetic Peptide

<400> SEQUENCE: 18

Phe Ser Ala Lys Val Glu Ala Ser Gly Phe Ser Val Thr Pro Thr Leu
1               5                   10                  15

Ala Val Tyr Ser Pro His Arg Leu Val Met Phe Ile Phe Ile Met Ile
            20                  25                  30

Arg Lys Lys His His Phe Leu Leu Trp Leu Tyr Ala Tyr Phe Met
        35                  40                  45

<210> SEQ ID NO 19
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 19

Phe Phe Gln Thr Leu Ile Leu Ser Met Gly Ser Val Lys Ser Ile Cys
1               5                   10                  15

Phe Pro Lys Val
            20

<210> SEQ ID NO 20
<211> LENGTH: 48
<212> TYPE: PRT
<213> ORGANISM: Artificial Sequence
<220> FEATURE:
<223> OTHER INFORMATION: Synthetic Peptide

<400> SEQUENCE: 20

Asn Ser Thr Gly Leu Ser Ala Ser Gln Ala Thr Ala Phe His Ser Gly
1               5                   10                  15

Leu His Pro Phe Lys Arg Gly Ile Asn Lys Val Lys Cys Ile Pro Gly
            20                  25                  30

Ser Val Ala Ala Gly Leu Thr Ser Met Ser Leu Gly Gly Gln Thr Ala
        35                  40                  45

<210> SEQ ID NO 21
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 21
```

```
Phe Phe Trp Gly Lys Ser Lys Tyr Tyr Ile Met Lys Thr Met Val Gly
1               5                   10                  15

Lys Trp Lys Met Ile Leu Phe Arg Pro Glu Leu Gly Leu Glu Ile Lys
                20                  25                  30

<210> SEQ ID NO 22
<211> LENGTH: 46
<212> TYPE: PRT
<213> ORGANISM: Artificial Sequence
<220> FEATURE:
<223> OTHER INFORMATION: Synthetic Peptide

<400> SEQUENCE: 22

Phe Met Ile Lys Glu Leu Glu Ala Ser Tyr Phe Lys Gly Ala Thr Gln
1               5                   10                  15

Ile Glu Cys Ile Glu Met Ala Lys Gln Pro Lys Gly Asp Pro Glu Leu
                20                  25                  30

Val Tyr Met Thr Val Lys Cys Lys Thr Val Lys Pro Val Ile
            35                  40                  45

<210> SEQ ID NO 23
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 23

Phe Pro Tyr Met Tyr Asn His Tyr Trp Val Lys Cys Glu Leu Ile Arg
1               5                   10                  15

Glu Phe Thr Leu Leu Lys Lys Val Asn Lys Tyr His Arg Ser Ser Arg
                20                  25                  30

Ile Trp Leu
        35
```